United States Patent
Yasuma et al.

(10) Patent No.: US 6,391,905 B1
(45) Date of Patent: May 21, 2002

(54) CONDENSED 4,5,6,7-TETRAHYDROBENZO [C]THIOPENES AS ENHANCER FOR CELL DIFFERENTIATION INDUCTION FACTOR ACTION

(75) Inventors: Tsuneo Yasuma; Tsuneo Oda, both of Ibaraki; Masatoshi Hazama; Shigehisa Taketomi, both of Ikeda, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/847,416

(22) Filed: May 3, 2001

Related U.S. Application Data

(62) Division of application No. 09/559,453, filed on Apr. 28, 2000, now Pat. No. 6,242,471, which is a division of application No. 09/252,913, filed on Feb. 19, 1999, now Pat. No. 6,066,658, which is a continuation of application No. PCT/JP97/03122, filed on Sep. 5, 1997.

(30) Foreign Application Priority Data

Sep. 6, 1996 (JP) .............................................. 8-237006

(51) Int. Cl.$^7$ ................... A61K 31/4162; C07D 231/00
(52) U.S. Cl. ..................................... 514/403; 548/359.5
(58) Field of Search ........................ 548/359.5; 514/403

(56) References Cited

FOREIGN PATENT DOCUMENTS

| JP | 08 175992 | 7/1996 |
| JP | 08 245386 | 9/1996 |

OTHER PUBLICATIONS

Augustin, et al., J. Prakt, Chem., vol. 321, No. 2, 1979, pp. 215–225.
Prim, et al., Liebigs Ann., No. 2, Feb. 1996, pp. 239–245.
Maybridge Chemical Co., Ltd. Catalogue, Oct. 1991, pp. 1–6.
van Rhee, et al., J. Med. Chem. 1996, vol. 39, No. 2, pp. 389–406.
Prim, et al., Synthetic Communications, 25(16), pp. 2449–2455 (1995).

*Primary Examiner*—Laura L. Stockton
(74) *Attorney, Agent, or Firm*—Fitzpatrick, Cella, Harper & Scinto

(57) ABSTRACT

A compound represented by the formula:

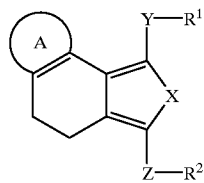

wherein X represents a sulfur atom or an oxygen atom; Y represents an optionally oxidized sulfur atom or an oxygen atom; Z represents a bond or a divalent hydrocarbon group; $R^1$ represents an optionally substituted hydrocarbon group; $R^2$ represents an optionally amidated or esterified carboxyl group; ring A represents an optionally substituted aromatic 5-membered heterocyclic ring; or a salt thereof.

A compound of the above formula possesses cell differentiation inducing factor action-enhancing activity and antimatrix metalloprotease activity and that is useful in the prevention and treatment of bone diseases such as osteoporosis, bone fractures, osteoarthritis and rheumatoid arthritis, arteriosclerosis, cancer metastasis, and diseases based on nerve degeneration.

13 Claims, 1 Drawing Sheet

5 ng/ml NGF 5 ng/ml NGF + 10 µM compound of Example 37

CONDENSED 4,5,6,7-TETRAHYDROBENZO [C]THIOPENES AS ENHANCER FOR CELL DIFFERENTIATION INDUCTION FACTOR ACTION

This application is a division of application Ser. No. 09/559,453 filed Apr. 28, 2000 now U.S. Pat. No. 6,242,471, which is a division of application Ser. No. 09/252,913 filed Feb. 19, 1999 now U.S. Pat. No. 6,066,658, which in turn is a continuation of PCT International Application No. PCT/JP97/03122 filed Sep. 5, 1997 designating the United States.

TECHNICAL FIELD

The present invention relates to a fused heterocyclic ring derivative acting to enhance the action of cell differentiation inducing factors such as bone morphogenetic protein and neurotrophic factors, and possessing anti-matrix metalloprotease (MMP) activity, a method of its production, and use thereof.

BACKGROUND ART

Osteoporosis is a pathologic state or disease involving some symptom or risk due to quantitative reduction in bone exceeding a certain degree. Major symptoms are spinal kyphosis, and fractures of dorsolumbar bones, vertebral centra, femoral necks, lower end of radius, ribs, upper end of humerus, and others. In bone tissue, osteogenesis and bone destruction by bone resorption are repeated with a good balance (bone remodelling); osteoblasts and osteoclasts play key roles in osteogenesis and bone resorption, respectively. Bone resorption surpassing osteogenesis, upon deterioration of the balance between osteogenesis and bone destruction by bone resorption, results in osteoporosis with a quantitative reduction in bone. Traditionally, bone resorption suppressors such as estrogens, calcitonin and bisphosphonates have been mainly used as prophylactic/therapeutic drugs for osteoporosis. However, these bone resorption suppressors fail to have a satisfactory effect in some cases, due to limitation on the subject or to uncertain efficacy. There is therefore a need for an osteogenesis promoter that serves as a prophylactic/therapeutic drug for osteoporosis to increase once-decreased bone mass.

Bone morphogenetic protein (BMP), isolated from decalcified bone, is the only group of protein factors known to be capable of ectopic bone induction. It is therefore useful as an osteogenesis promoter in bone healing, bone reconstruction etc. Also, because BMP directly promotes osteoblast differentiation, it is assumed to play a role as a coupling factor in bone remodelling, and is thought to be closely involved in bone metabolism. Also, it is known that the BMP content in bone matrix in aged animals has been considerably decreased, suggesting that BMP is profoundly involved in the maintenance of bone mass. This suggests that BMP is promising as a therapeutic drug for various bone diseases such as osteoporosis. However, because BMP is normally present in trace amounts in living body so that its supply is limited, and because BMP is a protein so that a problem arises in its administration, the target diseases to which it is applicable are limited.

In addition, BMP has been reported to possess an activity like that of neurotrophic factors [Journal of Cell Biology, Vol. 119, p. 1,721 (1992)]. Also, because it is known that the BMP gene is strongly expressed in brain tissue, and because BMP has been suggested as playing an important role in neural tube formation in embryogenesis, BMP is thought to be profoundly involved in the differentiation or functional maintenance of nerve cells.

Neurotrophic factors, a group of proteinous factors playing an important role in the survival and functional expression of nerve cells, include nerve growth factor (NGF), brain-derived neurotrophic factor (BDNF) and neurotrophin-3 (NT-3). NGF promotes the differentiation and maturation of the sympathetic ganglion cells and dorsal spinal root ganglion cells of the neural tube in the peripheral nervous system and acts on the cholinergic neuron cells of the septal field (procephalic basal ganglia) in the central nervous system. NGF is essential for the maintenance of nervous function even after completion of ferentiation. BDNF acts on the dorsal spinal root ganglion cells and nodal ganglion cells in the peripheral nervous system but does not act on sympathetic ganglion cells. On the other hand, in the central nervous system, BDNF acts on the cholinergic nerve cells and GABA (γ-aminobutyric acid)-acting nerve cells of the septal field, and the dopaminergic nerve cells of the mesencephalon. NT-3 is characterized by potent action on the sensory nerve cells derived from the neural plate, although its action overlaps those of NGF and BDNF in the peripheral nervous system.

Alzheimer dementia has been characterized by extensive disorder and loss of cerebral cortical nerve cells, as well as degeneration and loss of cholinergic neuron of basal forebrain, including the septum; NGF and new neurotrophic factors are considered as candidates for therapeutic drugs therefore. Also, for Parkinson's disease, a disease characterized by degeneration and loss of the mesencephalic dopaminergic nerve neuron, BDNF and GDNF (glial cell line-derived neurotrophic factors), neurotrophic factors for those nerve cells, are expected to serve as a therapeutic drug. Because these neurotrophic factors are proteins, however, their application are subject to limitation.

Osteoarthritis, a non-inflammatory disease based on articular cartilage degeneration, is irreversible and progressive, although its progression is slow. Spinal intervertebral degeneration is relatively common among males, while the incidence of knee joint degeneration is relatively high in females. Etiologically, systemic factors such as genetic predispositions, age, estrogen and obesity, and the local factor of mechanical load are involved. When articular cartilage begins to be destroyed by various causes, proteolytic enzymes, mainly metalloprotease and serine protease, are locally produced, whose action causes cartilage matrix lysis, resulting in cartilage cracking, abrasion, ulcer etc., which in turn lead to the exposure of the subcartilaginous plate and sometimes cause calcium pyrophosphate crystal deposition on the deformed articular cartilage surface. Clinical symptoms include pain, hydrarthrosis, limitation of range of joint motion, creaking sound and deformation. Although much remains unknown as to the mechanism of onset, it is known that production of collagenase and other matrix metalloproteases (MMPs) is induced by the cytokines produced by chondrocytes, macrophages and synovial cells, such as interleukin (IL)-1, IL-6 and tumor necrosis factor (TNF)-α, resulting in the collapse of articular cartilage. Drugs that inhibit the metalloprotease production induction by these cytokines are therefore expected to be effective as prophylactic/therapeutic drugs for osteoarthritis; however, there are no known drugs with such action, and conventional chemotherapies comprise nothing more than symptomatic therapies such as oral or topical administration of sedative anti-inflammatory drugs, and intra-articular injection of articular cartilage-protecting drugs such as aqueous solutions of hyaluronic acid.

DISCLOSURE OF INVENTION

The present invention provides a compound that enhances the action of cell differentiation induction factors, represented by BMP and neurotrophic factors, that is effective in the treatment and prevention of osteoporosis, bone fractures, and diseases based on nerve degeneration, such as Alzheimer's disease, cerebral vascular dementia, amyotrophic lateral sclerosis (Lou Gehrig disease), depression and diabetic peripheral neutopathy, that possesses anti-MMP activity, and that is effective in the treatment and prevention of diseases involved by MMP, such as osteoarthritis, rheumatoid arthritis, arteriosclerosis and cancer metastasis.

After extensive investigation in search of low-molecular compounds that enhance the action of cell differentiation induction factors, the present inventors found that the fused thiophene derivatives represented by general formulas (I) and (I') below specifically enhance the osteoblast and nerve cell differentiation by BMP and neurotrophic factors, and suppress the collagenase production by chondrocytes. The present inventors made further investigation based on this finding, and developed the present invention.

Accordingly, the present invention relates to:

(1) a compound represented by general formula (I'):

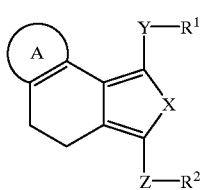

(I')

wherein X represents a sulfur atom or an oxygen atom; Y represents an optionally oxidized sulfur atom or an oxygen atom; Z represents a bond or a divalent hydrocarbon group; $R^1$ represents an optionally substituted hydrocarbon group; $R^2$ represents an optionally amidated or esterified carboxyl group; ring A represents an optionally substituted aromatic 5-membered heterocyclic ring; provided that when X and Y are both S,

does not represent

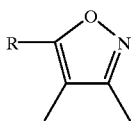

(R represents a hydrogen atom or a $C_{1-6}$ alkyl group); or a salt thereof, (2) the compound according to term (1) above wherein Y is a sulfur atom,
(3) the compound according to term (1) above wherein Z is a bond,
(4) the compound according to term (1) above wherein $R^1$ is a $C_{1-8}$ alkyl group, a $C_{6-10}$ aryl group or $C_{7-14}$ aralkyl group,
(5) the compound according to term (1) above wherein $R^2$ is a carboxyl group, a $C_{1-8}$ alkoxy-carbonyl group, a carbamoyl group, an N—($C_{1-8}$ alkyl)carbamoyl group, an N-[di($C_{1-6}$ alkoxy)phosphoryl-$C_{1-6}$ alkylphenyl] carbamoyl group or an N—($C_{1-8}$ alkyl), N—($C_{1-8}$ alkoxy)carbamoyl group,
(6) the compound according to term (1) above wherein $R^2$ is a carboxyl group, a carbamoyl group or an N—($C_{1-8}$ alkyl)carbamoyl group,
(7) the compound according to term (1) above wherein ring A is an optionally substituted thiazole ring, oxazole ring, imidazole ring or thiophene ring,
(8) the compound according to term (1) above wherein ring A is (i) a thiazole ring, oxazole ring or imidazole ring which may be substituted with a $C_{1-8}$ alkyl group, a $C_{6-10}$ aryl group or a $C_{6-10}$ aryl-$C_{2-4}$ alkenyl group, or (ii) a thiophene ring which may be substituted with a carboxyl group, a $C_{1-8}$ alkoxy-carbonyl group, a carbamoyl group, an N—($C_{1-8}$ alkyl)carbamoyl group, an N-[di($C_{1-6}$ alkoxy)phosphoryl-$C_{1-6}$ alkylphenyl] carbamoyl group or a $C_{6-10}$ aryl group,
(9) the compound according to term (1) above wherein ring A is (i) a thiazole ring, oxazole ring or imidazole ring substituted with a $C_{1-8}$ alkyl group, a $C_{6-10}$ aryl group or a $C_{6-10}$ aryl-$C_{2-4}$ alkenyl group, or (ii) a thiophene ring substituted with a $C_{1-8}$ alkoxy-carbonyl group,
(10) the compound according to term (1) above wherein ring A is a thiazole ring or oxazole ring substituted with a $C_{1-8}$ alkyl group or a $C_{6-10}$ aryl group,
(11) the compound according to term (1) above wherein X is a sulfur atom or an oxygen atom, Y is a sulfur atom, Z is a bond, $R^1$ is a $C_{1-8}$ alkyl group, a $C_{6-10}$ aryl group or a $C_{7-14}$ aralkyl group, $R^2$ is a carboxyl group, a $C_{1-8}$ alkoxy-carbonyl group, a carbamoyl group, an N—($C_{1-6}$ alkyl)carbamoyl group, an N-[di($C_{1-6}$ alkoxy)phosphoryl-$C_{1-6}$ alkylphenyl]carbamoyl group or an N—($C_{1-8}$ alkyl), N—($C_{1-8}$ alkoxy)carbamoyl group, ring A is (i) a thiazole ring, oxazole ring or imidazole ring substituted with a $C_{1-8}$ alkyl group, a $C_{6-10}$ aryl group or a $C_{6-10}$ aryl-$C_{2-4}$ alkenyl group, or (ii) a thiophene ring substituted with a $C_{1-8}$ alkoxy-carbonyl group,
(12) the compound according to term (1) above which is 4,5-dihydro-8-methylthio-2-phenylfuro[3,4-e] benzothiazole-6-carboxylic acid, 4,5-dihydro-2-methyl-8-methylthiothieno[3,4-e]benzothiazole-6-carboxamide, 4,5-dihydro-2-methyl-8-methylthiothieno[3,4-g]benzoxazole-6-carboxamide, 4,5-dihydro-8-isopropylthio-2-methylthieno[3,4-g] benzoxazole-6-carboxamide, N-ethyl-4,5-dihydro-8-methylthio-2-phenylthieno[3,4-e]benzothiazole-6-carboxamide, N-(3,4-methylenedioxybenzyl)-4,5-dihydro-8-methylthio-2-phenylthieno[3,4-e] benzothiazole-6-carboxamide, N-(4-pyridylmethyl)-4,5-dihydro-8-methylthio-2-phenylthieno[3,4-e] benzothiazole-6-carboxamide, N-(3-pyridyl)-4,5-dihydro-8-methylthio-2-phenylthieno[3,4-e] benzothiazole-6-carboxamide, N-methoxy-N-methyl-4,5-dihydro-8-methylthio-2-phenylthieno[3,4-e] benzothiazole-6-carboxamide, or a salt thereof,

(13) a compound of the formula (I"):

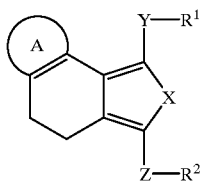

(I")

wherein X represents a sulfur atom or an oxygen atom; Y represents an optionally oxidized sulfur atom or an oxygen atom; Z represents a bond or a divalent hydrocarbon group; $R^1$ represents an optionally substituted hydrocarbon group; $R^2$ represents an optionally amidated or esterified carboxyl group; ring A represents an optionally substituted aromatic 5-membered heterocyclic ring; but excluding the compound

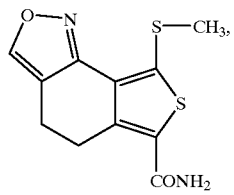

(14) a pharmaceutical composition which comprises an effective amount of the compound according to term (1) above and a pharmaceutically acceptable salt,
(15) the pharmaceutical composition according to term (14) above which is for prophylaxis or treatment of osteoporosis, bone fractures, osteoarthritis, rheumatoid arthritis, arteriosclerosis, cancer metastasis or a disease based on neural degeneration,
(16) an anti-matrix metalloprotease agent which comprises a compound represented by general formula (I):

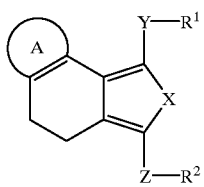

(I)

wherein X represents a sulfur atom or an oxygen atom; Y represents an optionally oxidized sulfur atom or an oxygen atom; Z represents a bond or a divalent hydrocarbon group; $R^1$ represents an optionally substituted hydrocarbon group; $R^2$ represents an optionally amidated or esterified carboxyl group; ring A represents an optionally substituted aromatic 5-membered heterocyclic ring; or a salt thereof,
(17) an enhancer for cell differentiation induction factor action containing the compound according to term (1) above,
(18) use of a compound of the formula (I) for manufacturing a pharmaceutical composition,
(19) a method which comprises administering an effective amount of a compound of the formula (I) in a pharmaceutically acceptable carrier to provide a prophylactic or therapeutic action for osteoporosis, fracture, osteoarthritis, rheumatoid arthritis, arterial sclerosis, cancer transfer or a disease based on degenerative nerve in warm blooded animals, and
(20) a method of producing a compound represented by the general formula:

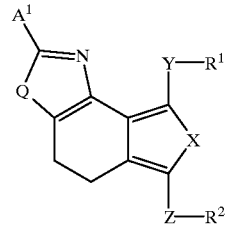

wherein Q represents a sulfur atom, an oxygen atom or NH; $A^1$ represents a hydrogen atom or an optionally substituted hydrocarbon group; X represents a sulfur atom or an oxygen atom; Y represents an optionally substituted sulfur atom or an oxygen atom; Z represents a bond or a divalent hydrocarbon group; $R^1$ represents an optionally substituted hydrocarbon group; $R^2$ represents an optionally amidated or esterified carboxyl group; or a salt thereof, which comprises reacting a compound represented by the general formula:

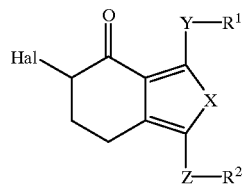

wherein Hal represents a halogen atom; and the other symbols have the same definitions as those shown above; or a salt thereof;
with a compound represented by the general formula:

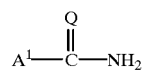

wherein the symbols have the same definitions as those shown above; or a salt thereof.

With respect to general formulas (I), (I') and (I") [hereinafter together referred to as general formula (I)], X represents a sulfur atom (S) or an oxygen atom (O).

With respect to general formula (I), Y represents a sulfur atom that may be oxidized (S, SO, $SO_2$) or an oxygen atom (O). Y is preferably a sulfur atom.

With respect to general formula (I), Z represents a bond or a divalent hydrocarbon group. Examples of divalent hydrocarbon groups include, for example, saturated or unsaturated divalent hydrocarbon groups having 1 to 3 carbon atoms, such as —$(CH_2)_n$— (n represents an integer from 1 to 3), —CH=CH—, —CH=CHCH$_2$—, —CH$_2$CH=CH—, —C≡C—, —C≡CCH$_2$— and —CH$_2$C≡C— (e.g., alkylenes, alkenylenes, alkynylenes). Z is preferably a bond.

With respect to general formula (I), the hydrocarbon represented by $R^1$, which may be substituted, is exemplified by aliphatic hydrocarbon groups which may be substituted, alicyclic hydrocarbon groups which may be substituted, alicyclic-aliphatic hydrocarbon groups which may be substituted, aromatic hydrocarbon groups which may be substituted, and aromatic-aliphatic hydrocarbon groups (aralkyl groups) which may be substituted. Such aliphatic hydrocarbon groups include saturated aliphatic hydrocarbon groups (e.g., alkyl groups) having 1 to 8 carbon atoms, such as methyl, ethyl, propyl, isopropyl, butyl, isobutyl, sec-butyl, tert-butyl, pentyl, isopentyl, neopentyl, tert-pentyl, hexyl, isohexyl, heptyl and octyl; and unsaturated aliphatic hydrocarbon groups (e.g., alkenyl groups, alkynyl groups, alkadienyl groups, alkadiynyl groups) having 2 to 8 carbon atoms, such as vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 2,4-hexadienyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl, 1-heptynyl and 1-octynyl. Such alicyclic hydrocarbon groups include saturated alicyclic hydrocarbon groups (e.g., cycloalkyl groups) having 3 to 7 carbon atoms, such as cyclopropyl, cyclobutyl, cyclopentyl, cyclohexyl and cycloheptyl; unsaturated alicyclic hydrocarbon groups (e.g., cycloalkenyl groups, cycloalkadienyl groups) having 3 to 7 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl; and partially saturated condensed bicyclic hydrocarbon groups such as 1-indenyl, 2-indenyl, 1-indanyl, 2-indanyl, 1,2,3,4-tetrahydro-1-naphthyl, 1,2,3,4-tetrahydro-2-naphthyl, 1,2-dihydro-1-naphthyl, 1,2-dihydro-2-naphthyl, 1,4-dihydro-1-naphthyl, 1,4-dihydro-2-naphthyl, 3,4-dihydro-1-naphthyl and 3,4-dihydro-2-naphthyl. Such alicyclic-aliphatic hydrocarbon groups include groups resulting from the binding of one of the above-mentioned alicyclic hydrocarbon groups and one of the above-mentioned aliphatic hydrocarbon groups, and having 4 to 14 carbon atoms (e.g., $C_{3-7}$ cycloalkyl-$C_{1-4}$ alkyl groups, $C_{3-7}$ cycloalkenyl-$C_{1-4}$ alkyl groups, $C_{3-7}$ cycloalkyl-$C_{2-4}$ alkenyl groups, $C_{3-7}$ cycloalkenyl-$C_{2-4}$ alkenyl groups, $C_{9-10}$ partially saturated condensed bicyclic hydrocarbon-$C_{1-4}$ alkyl groups, $C_{9-10}$ partially saturated condensed bicyclic hydrocarbon-$C_{2-4}$ alkenyl groups) such as cyclopropylmethyl, cyclopropylethyl, cyclobutylmethyl, cyclobutylethyl, cyclopentylmethyl, 2-cyclopentenylmethyl, 3-cyclopentenylmethyl, cyclopentylethyl, cyclohexylmethyl, 2-cyclohexenylmethyl, 3-cyclohexenylmethyl, cyclohexylethyl, cycloheptylmethyl, cycloheptylethyl, 2-(3,4-dihydro-2-naphthyl)ethyl, 2-(1,2,3,4-tetrahydro-2-naphthyl)ethyl and 2-(3,4-dihydro-2-naphthyl)ethenyl. Such aromatic hydrocarbon groups include aryl groups having 6 to 10 carbon atoms, such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl and 5,6-dihydro-4-naphthyl. Such aromatic-aliphatic hydrocarbon groups include phenyl-$C_{1-4}$ alkyl groups such as benzyl, phenethyl, 1-phenylethyl, 1-phenylpropyl, 2-phenylpropyl and 3-phenylpropyl, aralkyl groups having 7 to 14 carbon atoms ($C_{6-10}$ aryl-$C_{1-4}$ alkyl groups) such as naphthyl-$C_{1-4}$ alkyl groups, e.g., α-naphthylmethyl, α-naphthylethyl, β-naphthylmethyl and β-naphthylethyl, and $C_{6-10}$ aryl-$C_{2-4}$ alkenyl groups such as phenyl-$C_{2-4}$ alkenyl groups, e.g., styryl and cinnamyl.

Said hydrocarbon group may be substituted with 1 to 3 substituents. Such substituents include, for example, lower ($C_{1-6}$) alkyl groups (e.g., methyl, ethyl, propyl, isopropyl, butyl, isobutyl, sec-butyl, tert-butyl, pentyl, isopentyl, neopentyl, hexyl), lower ($C_{2-6}$) alkenyl groups (e.g., vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl), lower ($C_{2-6}$) alkynyl groups (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl), $C_{3-7}$ cycloalkyl groups (e.g., cyclopropyl, cyclobutyl, cyclopentyl, cyclohexyl, cycloheptyl), $C_{6-10}$ aryl groups (e.g., phenyl, α-naphthyl, β-naphthyl), aromatic heterocyclic groups [(i) aromatic 5- or 6-membered heterocyclic groups having 1 to 4 hetero atoms selected from nitrogen atoms, oxygen atoms and sulfur atoms, (ii) fused bicyclic heterocyclic groups resulting from fusion of an aromatic 5- or 6-membered heterocyclic ring having 1 to 3 hetero atoms selected from nitrogen atoms, oxygen atoms and sulfur atoms, and a benzene ring or an aromatic 5- or 6-membered heterocyclic ring having 1 to 3 hetero atoms selected from nitrogen atoms, oxygen atoms and sulfur atoms, (iii) fused tricyclic heterocyclic groups resulting from fusion of an aromatic 5- or 6-membered heterocyclic ring having 1 to 3 hetero atoms selected from nitrogen atoms, oxygen atoms and sulfur atoms, a benzene ring and an aromatic 5- or 6-membered heterocyclic ring having 1 to 3 hetero atoms selected from nitrogen atoms, oxygen atoms and sulfur atoms or a benzene ring, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl], non-aromatic heterocyclic groups (e.g., 4- to 7-membered non-aromatic heterocyclic groups having 1 to 3 hetero atoms selected from nitrogen atoms, oxygen atoms and sulfur atoms, such as oxylanyl, azetidinyl, oxetanyl, thietanyl, pyrrolidinyl, tetrahydrofuryl, thiolanyl, piperidinyl, tetrahydropyranyl, morpholinyl, thiomorpholinyl and piperazinyl), $C_{7-14}$ aralkyl groups (e.g., $C_{6-10}$ aryl-$C_{1-4}$ alkyl groups such as benzyl, phenethyl, 1-phenylethyl, 1-phenylpropyl, 2-phenylpropyl, 3-phenylpropyl, α-naphthylmethyl, α-naphthylethyl, β-naphthylmethyl and β-naphthylethyl), amino groups, N-monosubstitutional amino groups [e.g., N—($C_{1-6}$ alkyl)amino groups such as methylamino, ethylamino, allylamino, cyclohexylamino and phenylamino, N—($C_{2-6}$ alkenyl)amino groups, N—($C_{3-7}$ cycloalkyl)amino groups and N—($C_{6-10}$ aryl)amino groups), N,N-disubstitutional amino groups [e.g., amino groups substituted with 2 substituents selected from $C_{1-6}$ alkyl groups, $C_{2-6}$ alkenyl groups, $C_{3-7}$ cycloalkyl groups and $C_{6-10}$ aryl groups, such as dimethylamino, diethylamino, dibutylamino, diallylamino and N-methyl-N-phenylamino), amidino groups, acyl groups (e.g., $C_{2-8}$ alkanoyl groups such as acetyl, propionyl, butyryl, isobutyryl, valeryl, isovaleryl, pivaloyl, hexanoyl, heptanoyl, octanoyl, cyclopropanecarbonyl, cyclobutanecarbonyl, cyclopentanecarbonyl, cyclohexanecarbonyl, crotonoyl, 2-cyclohexenecarbonyl, benzoyl and nicotinoyl, $C_{3-8}$ alkenoyl groups, $C_{3-7}$ cycloalkyl-carbonyl groups, $C_{3-7}$ cycloalkenyl-carbonyl groups, $C_{6-10}$ aryl-carbonyl groups, heterocyclic-carbonyl groups resulting from binding of a 5- or 6-membered aromatic or non-aromatic 5- or 6-membered heterocyclic ring having 1 to 3 hetero atoms selected from nitrogen atoms, oxygen atoms and sulfur atoms, and a carbonyl group), carbamoyl groups, N-monosubstitutional carbamoyl groups, [e.g., N—($C_{1-6}$ alkyl)carbamoyl groups such as methylcarbamoyl, ethylcarbamoyl, cyclohexylcarbamoyl and phenylcarbamoyl, N—($C_{2-6}$ alkenyl)carbamoyl groups, N—($C_{3-7}$ cycloalkyl)carbamoyl groups, N—($C_{6-10}$ aryl)carbamoyl groups], N,N-disubstitutional carbamoyl groups [e.g., carbamoyl groups substituted for by 2 substituents selected from $C_{1-6}$ alkyl groups, $C_{2-6}$ alkenyl groups, $C_{3-7}$ cycloalkyl groups and $C_{6-10}$ aryl groups, such as dimethylcarbamoyl, diethylcarbamoyl, dibutylcarbamoyl, diallylcarbamoyl, N-methyl-N-phenylcarbamoyl], sulfamoyl groups, N-monosubstitutional sulfamoyl groups [e.g., N—($C_{1-6}$ alkyl)sulfamoyl groups such as methylsulfamoyl, ethylsulfamoyl, cyclohexylsulfamoyl and phenylsulfamoyl, N—($C_{2-6}$ alkenyl)sulfamoyl groups, N—($C_{3-7}$ cycloalkyl) sulfamoyl groups, N—($C_{6-10}$ aryl)sulfamoyl groups], N,N-disubstitutional sulfamoyl groups [e.g., sulfamoyl groups substituted for by 2 substituents selected from $C_{1-6}$ alkyl groups, $C_{2-6}$ alkenyl groups, $C_{3-7}$ cycloalkyl groups and $C_{6-10}$ aryl groups, such as dimethylsulfamoyl, diethylsulfamoyl, dibutylsulfamoyl, diallylsulfamoyl and N-methyl-N-phenylsulfamoyl], carboxyl groups, lower ($C_{1-6}$) alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl), hydroxyl groups, lower ($C_{1-6}$) alkoxy groups (e.g., methoxy, ethoxy, propoxy, isopropoxy, butoxy, isobutoxy, sec-butoxy, tert-butoxy, pentyloxy, hexyloxy), lower ($C_{2-6}$) alkenyloxy groups (e.g., allyloxy, 2-butenyloxy, 2-pentenyloxy, 3-hexenyloxy), $C_{3-7}$ cycloalkyloxy groups (e.g., cyclopropyloxy, cyclobutyloxy, cyclopentyloxy, cyclohexyloxy, cycloheptyloxy), $C_{6-10}$ aryloxy groups (e.g., phenoxy, naphthyloxy), $C_{7-14}$ aralkyloxy groups (e.g., $C_{6-10}$ aryl-$C_{1-4}$ alkyloxy groups such as phenyl-$C_{1-4}$ alkyloxys and naphthyl-$C_{1-4}$ alkyloxys), mercapto groups, lower ($C_{1-6}$) alkylthio groups (e.g., methylthio, ethylthio, propylthio, isopropylthio, butylthio, isobutylthio, sec-butylthio, tert-butylthio, pentylthio, isopentylthio, neopentylthio, hexylthio), $C_{7-14}$ aralkylthio groups (e.g., $C_{6-10}$ aryl-$C_{1-4}$ alkylthio groups such as phenyl-$C_{1-4}$ alkylthios and naphthyl-$C_{1-4}$ alkylthios), $C_{6-10}$ arylthio groups (e.g., phenylthio, naphthylthio), lower ($C_{1-6}$) alkylsulfinyl groups (e.g., methylsulfinyl, ethylsulfinyl, propylsulfinyl, isopropylsulfinyl, butylsulfinyl, isobutyl-sulfinyl, sec-butylsulfinyl, tert-butylsulfinyl, pentylsulfinyl, isopentylsulfinyl, neopentylsulfinyl, hexylsulfinyl), $C_{7-14}$ aralkylthio groups (e.g., $C_{6-10}$ aryl-$C_{1-4}$ alkylsulfinyl groups such as phenyl-$C_{1-4}$ alkylsulfinyls and naphthyl-$C_{1-4}$ alkylsulfinyls), $C_{6-10}$ arylsulfinyl groups (e.g., phenylsulfinyl, naphthylsulfinyl), lower ($C_{1-6}$) alkylsulfonyl groups (e.g., methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, hexylsulfonyl), $C_{7-14}$ aralkylsulfonyl groups (e.g., $C_{6-10}$ aryl-$C_{1-4}$ alkylsulfonyl groups such as phenyl-$C_{1-4}$ alkylsulfonyls and naphthyl-$C_{1-4}$ alkylsulfonyls), $C_{6-10}$ arylsulfonyl groups (e.g., phenylsulfonyl, naphthylsulfonyl), sulfo groups, cyano groups, azide groups, halogen atoms (e.g., fluorine, chlorine, bromine, iodine), nitro groups, nitroso groups, phosphono groups that may be esterified [e.g., phosphono groups, ($C_{1-6}$) alkoxy)phosphoryl groups such as ethoxyphosphoryl, di($C_{1-6}$ alkoxy)phosphoryl groups such as diethoxyphosphoryl], and lower ($C_{1-6}$)alkyl groups substituted for by phosphono groups that may be esterified (e.g., phosphono-$C_{1-6}$ alkyl groups, $C_{1-6}$ alkoxyphosphoryl-$C_{1-6}$ alkyl groups, di($C_{1-6}$ alkoxy)phosphoryl-$C_{1-6}$ alkyl groups such as diethoxyphosphorylmethyl).

The above-mentioned $C_{6-10}$ aryl groups, aromatic heterocyclic groups, $C_{6-10}$ aryl groups as substituents for N-monosubstitutional amino groups, $C_{6-10}$ aryl groups as substituents for N,N-disubstitutional amino groups, $C_{6-10}$ aryl groups as substituents for N-monosubstitutional carbamoyl groups, $C_{6-10}$ aryl groups as substituents for N,N-disubstitutional carbamoyl groups, $C_{6-10}$ aryls as substituents for N-monosubstitutional sulfamoyl groups, $C_{6-10}$ aryl groups as substituents for N,N-disubstitutional sulfamoyl groups, $C_{6-10}$ aryl groups in $C_{6-10}$ aryloxy groups, $C_{6-10}$ aryl groups in $C_{7-14}$ aralkyloxy groups, $C_{6-10}$ aryl groups it $C_{7-14}$ aralkylthio groups, $C_{6-10}$ aryl groups in $C_{6-10}$ arylthio groups, $C_{6-10}$ aryl groups in $C_{7-14}$ aralkylsulfinyl groups, $C_{6-10}$ aryl groups in $C_{7-14}$ aralkylsulfonyl groups, and $C_{6-10}$ aryl groups in $C_{6-10}$ arylsulfonyl groups may be further substituted with 1 to 3 substituents. Such substituents include, for example, lower ($C_{1-6}$)alkyl groups, amino groups, N—($C_{1-6}$ alkyl)amino groups, N,N-di($C_{1-6}$ alkyl) amino groups, amidino groups, carbamoyl groups, N—($C_{1-6}$ alkyl)carbamoyl groups, N,N-di($C_{1-6}$ alkyl)carbamoyl groups, sulfamoyl groups, N—($C_{1-6}$ alkyl)sulfamoyl groups, N—N-di($C_{1-6}$ alkyl)sulfamoyl groups, carboxyl groups, lower ($C_{2-7}$)alkoxycarbonyl groups, hydroxyl groups, lower ($C_{1-6}$)alkoxy groups, mercapto groups, lower ($C_{1-6}$)alkylthio groups, sulfo groups, cyano groups, azide groups, halogen atoms, nitro groups, nitroso groups, phosphono groups that may be esterified [e.g., phosphono groups, $C_{1-6}$ alkoxyphosphoryl groups, di($C_{1-6}$ alkoxy)phosphoryl groups], and lower ($C_{1-6}$)alkyl groups substituted with phosphono groups that may be esterified [e.g., phosphono-$C_{1-6}$ alkyl groups, $C_{1-6}$ alkoxyphosphoryl-$C_{1-6}$ alkyl groups, di($C_{1-6}$ alkoxy) phosphoryl-$C_{1-6}$ alkyl groups such as diethoxyphosphorylmethyl].

$R^2$ represents a carboxyl group that may be amidated or esterified, and is exemplified by groups represented by the formula:

—COOR$^3$ wherein $R^3$ represents a hydrogen atom or a hydrocarbon group that may be substituted for, and groups represented by the formula:

—CON($R^4$)($R^5$)

wherein $R^4$ and $R^5$ each represent a hydrogen atom or a hydrocarbon group that may be substituted for.

The hydrocarbon group represented by $R^3$, $R^4$ or $R^5$, which may be substituted, is exemplified by the same groups as the hydrocarbon groups represented by $R^1$ above, which may be substituted.

Ring A represents an aromatic 5-membered heterocyclic ring that may be substituted. Aromatic 5-membered heterocyclic rings include, for example, azole rings and thiophene rings that contain 1 or 2 nitrogen atoms as hetero atoms and that may contain 1 hetero atom selected from an oxygen atom and a sulfur atom, such as pyrrole rings, oxazole rings, thiazole rings, imidazole rings, pyrazole rings, isoxazole rings, isothiazole rings and thiadiazole rings.

Such thiazole rings may have 1 or 2 substituents; such substituents include, for example, the same groups as the hydrocarbon groups represented by $R^1$ above, which may be substituted. Such thiophene rings may have 1 substituent; said substituent is exemplified by the same groups as the carboxyl groups represented by $R^2$ above, which may be amidated or esterified.

is preferably a group represented by

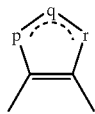

wherein —p—q—r— represents —O—C($A^1$)=N—, —S—C($A^1$)=N—, —N($A^2$)—C($A^1$)=N—, —N=C($A^1$)—N($A^2$)—, —N=C($A^1$)—O—, —N=C($A^1$)—S—, —CH=N—O—, —CH=N—N($A^2$)—, —CH=N—S—, —S—N=N—, —N($A^2$)—CH=CH— or —CH=C($A^3$)—S—; $A^1$ and $A^2$ each represent a hydrogen atom or a hydrocarbon group that may be substituted; $A^3$ represents a hydrogen atom or a carboxyl group that may be amidated or esterified.

The hydrocarbon group represented by $A^1$ or $A^2$, which may be substituted, is exemplified by the same groups as the hydrocarbon groups represented by $R^1$ above, which may be substituted. The carboxyl group represented by $A^3$, which may be amidated or esterified, is exemplified by the same groups as the carboxyl groups represented by $R^2$ above, which may be amidated or esterified.

$A^1$ is preferably a hydrocarbon group that may be substituted; $A^2$ is preferably a hydrogen atom; $A^3$ is preferably a carboxyl group that may be amidated or esterified.

Regarding the compound of the present invention, represented by the general formula (I), stereoisomers or optical isomers may be present, depending on the kind of substituent; such isomers and mixtures thereof are also included in the scope of the present invention.

The salt of the compound of the present invention, represented by general formula (I), is preferably a pharmaceutically acceptable salt, exemplified by salts with inorganic bases, salts with organic bases, salts with inorganic acids, salts with organic acids, and salts with basic or acidic amino acids. Preferable salts with inorganic bases include, for example, alkali metal salts such as sodium salt and potassium salt; alkaline earth metal salts such as calcium salt and magnesium salt; and aluminum salt and ammonium salt. Preferable salts with organic bases include, for example, salts with trimethylamine, triethylamine, pyridine, picoline, ethanolamine, diethanolamine, triethanolamine, dicyclohexylamine, N,N'-dibenzylethylenediamine etc. Preferable salts with inorganic acids include, for example, salts with hydrochloric acid, hydrobromic acid, nitric acid, sulfuric acid, phosphoric acid etc. Preferable salts with organic acids include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc. Preferable salts with basic amino acids include, for example, salts with arginine, lysine, ornithine etc. Preferable salts with acidic amino acids include, for example, salts with aspartic acid, glutamic acid etc.

Also, the salts of compounds represented by general formula (I) include the hydrates of compounds represented by general formula (I).

The compound of the present invention, represented by general formula (I), or a salt thereof, can be administered orally or non-orally, singly or as formulated with a pharmaceutically acceptable carrier, in the form of solid preparations such as tablets, capsules, granules and powders, or liquid preparations such as syrups and injectable preparations. The compound represented by general formula (I) or a salt thereof can be prepared as a pharmaceutical preparation normally wherein it is normally contained at 0.5 to 100% (w/w) by a conventional method. Pharmaceutically acceptable carriers are various organic or inorganic carrier substances in common use as pharmaceutical materials, including excipients, lubricants, binders and disintegrants for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary. Preferable excipients include, for example, lactose, sucrose, D-mannitol, starch, crystalline cellulose and light silicic anhydride. Preferable lubricants include, for example, magnesium stearate, calcium stearate, talc and colloidal silica. Preferable binders include, for example, crystalline cellulose, sucrose, D-mannitol, dextrin, hydroxypropyl cellulose, hydroxypropylmethyl cellulose and polyvinylpyrrolidone. Preferable disintegrants include, for example, starch, carboxymethyl cellulose, carboxymethyl cellulose calcium, crosscalmelose sodium and carboxymethyl starch sodium. Preferable solvents include, for example, water for injection, ethanol, propylene glycol, macrogol, sesame oil and corn oil. Preferable dissolution aids include, for example, polyethylene glycol, propylene glycol, D-mannitol, benzyl benzoate, ethanol, tris(hydroxymethyl) aminomethane, cholesterol, triethanolamine, sodium carbonate and sodium citrate. Preferable suspending agents include, for example, surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include, for example, sodium chloride, glycerol and D-mannitol. Preferable buffers include, for example, buffer solutions of phosphates, acetates, carbonates, citrates etc. Preferable soothing agents include, for example, benzyl alcohol. Preferable preservatives include, for example, p-oxybenzoic acid esters, chlorobutanol, benzyl alcohol, phenethyl alcohol, dehydroacetic acid and sorbic acid. Preferable antioxidants include, for example, sulfites and ascorbic acid.

The present invention further provides a method of producing a compound represented by general formula (I) or a salt thereof. In the reactions below, when the starting compound has an amino group, a carboxyl group or a hydroxyl group as a substituent, these groups may incorporate a protecting group in common use in peptide chemistry and other fields; the desired compound can be obtained by removing the protecting group after reaction as necessary. Useful amino group-protecting groups include, for example, $C_{1-6}$ alkanoyls that may be substituted (e.g., formyl, acetyl, propionyl, butyryl), benzoyl, $C_{2-6}$ alkoxycarbonyls (e.g., methoxycarbonyl, ethoxycarbonyl), phenoxycarbonyls, $C_{7-14}$ aralkyloxycarbonyls (e.g., phenyl-$C_{2-4}$ alkoxycarbonyls such as benzyloxycarbonyl), trityl and phthaloyl. Substituents for these protecting groups include, for example, halogen atoms (e.g., fluorine, chorine, bromine, iodine), $C_{1-6}$ alkanoyls (e.g., formyl, acetyl, propionyl, butyryl) and nitro groups, the number of substituents being about 1 to 3. Useful carboxyl group-protecting groups include, for example, $C_{1-6}$ alkyls that may have a substituent (e.g., methyl, ethyl, propyl, isopropyl, butyl, tert-butyl), phenyl, trityl and silyl. Substituents for these protecting groups include, for example, halogen atoms (e.g., fluorine, chorine, bromine, iodine), $C_{1-6}$ alkanoyls (e.g., formyl, acetyl, propionyl, butyryl) and nitro groups, the number of substituents being about 1 to 3. Useful hydroxyl group-protecting groups include, for example, $C_{1-6}$ alkyls that may have a substituent (e.g., methyl, ethyl, propyl, isopropyl, butyl, tert-butyl), phenyl, $C_{7-14}$ aralkyls (e.g., phenyl-$C_{1-4}$ alkyls such as benzyl), $C_{1-6}$ alkanoyls (e.g., formyl, acetyl, propionyl, butyryl), phenoxycarbonyl, $C_{7-14}$ aralkyloxycarbonyls (e.g., phenyl-$C_{2-4}$ alkoxycarbonyls such as benzyloxycarbonyl), pyranyl, furanyl and silyl. Substituents for these protecting groups include, for example, halogen atoms (e.g., fluorine, chorine, bromine, iodine), $C_{1-6}$ alkyls, phenyls, $C_{7-14}$ aralkyls (e.g., benzyl) and nitro groups, the number of substituents being about 1 to 4. Protecting group introduction and removal can be achieved by commonly known methods or methods based thereon (e.g., method described in Protective Groups in Organic chemistry, J. F. W. McOmie et al., Prenam Press)].

Method A

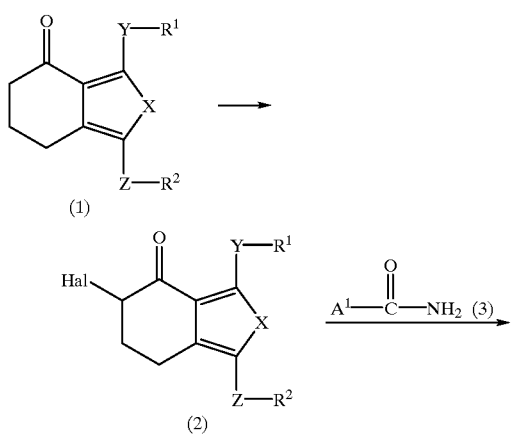

-continued

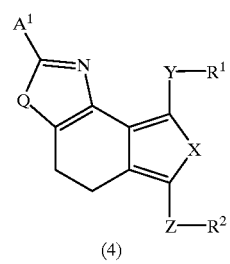

(4)

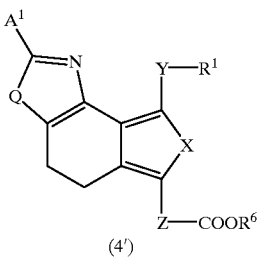

(4')

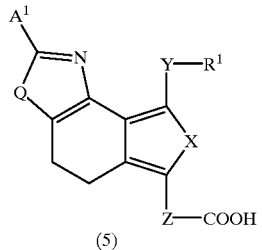

NHR⁴R⁵ (6)

(5)

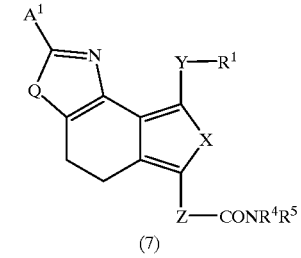

(7)

In case of Q=NH

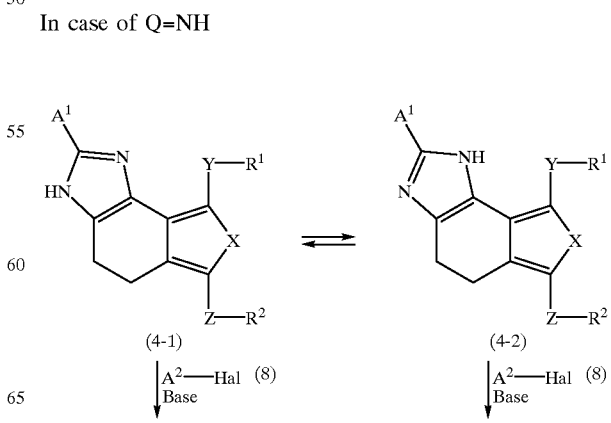

-continued

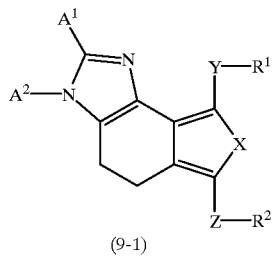

(9-1)

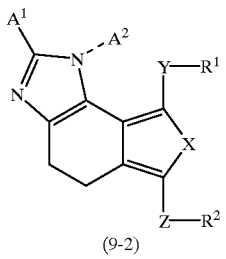

(9-2)

[In the above formulas, $R^6$ represents a hydrocarbon group that corresponds to $R^3$ and that may be substituted; Hal represents a halogen atom (e.g., fluorine, chlorine, bromine, iodine); Q represents a sulfur atom, an oxygen atom or an NH group; the other symbols have the same definitions as those shown above.]

In this method, a compound represented by general formula (1) is first halogenated to compound (2) by a commonly known method, then reacted with an amide, thioamide or amidine represented by general formula (3) to yield compound (4). The reaction of compounds (2) and (3) is carried out in an appropriate solvent in the presence or absence of a base. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane, alcohols such as methanol, ethanol, propanol, isopropanol, butanol, 2-methoxyethanol and ethylene glycol, N,N-dimethylformamide, dimethyl sulfoxide, acetonitrile, ethyl acetate and mixtures thereof. Said base is exemplified by bases selected as appropriate from alkali metal hydroxides such as sodium hydroxide and potassium hydroxide, alkaline earth metal hydroxides such as magnesium hydroxide and calcium hydroxide, alkali metal alkoxides such as sodium methoxide, sodium ethoxide and potassium tert-butoxide, alkali metal salts such as sodium carbonate, potassium carbonate, sodium hydrogen carbonate, potassium hydrogen carbonate, sodium acetate and potassium acetate, alkali metal hydrogen phosphates such as disodium hydrogen phosphate and dipotassium hydrogen phosphate, alkali metal hydrides such as soidum hydride and potassium hydride, and amines such as trimethylamine, triethylamine, pyridine, picoline, N-methylpyrrolidine, N-methylmorpholine and N,N-dimethylaniline. The amount of base used is preferably about 0 to about 5 mol equivalents per mol equivalent of compound (2); the amount of amide or thioamide, amidine (3) used is preferably about 1 to about 5 mol equivalents per mol equivalent of compound (2). This reaction is normally carried out at about 0° C. to about +180° C., preferably about +30° C. to +120° C., over a period of about 30 minutes to about 50 hours. Compound (4) thus obtained may be isolated and purified by known means of separation and purification such as concentration, concentration under reduced pressure, solvent extraction, crystallization, recrystallization, redissolution and chromatography.

By subjecting compound (4) wherein $R^2$ is —COOR$^6$ [i.e., compound (4')] to a commonly known acid or alkali hydrolysis reaction, corresponding carboxylic acid (5) can be produced; also, by subjecting compound (5) to a commonly known amidation reaction [reaction with compound (6)], compound (7) can be produced. Said amidation reaction can be carried out by reacting compound (5) with compound (6) after being converted to an acid halide with a halogenating agent such as oxalyl chloride or thionyl chloride. The reaction of compound (5) and halogenating agent is normally carried out in a solvent. Said solvent is exemplified by aromatic hydrocarbons such as benzene and toluene, and ethers such as diethyl ether and tetrahydrofuran. As a reaction promoter, pyridine, N,N-dimethylformamide, or the like, for example, may be used. This reaction is normally carried out at about 0° C. to about +120° C. over a period of about 30 minutes to about 24 hours. The amount of halogenating agent used is preferably about 1 to 2 mol equivalents per mol equivalent of compound (5). The acid halide thus obtained may be subjected to a reaction with compound (6) after being separated by an ordinary means of separation and purification. Alternatively, the reaction mixture, containing said acid halide, may be subjected to a reaction with compound (6) without separation. The reaction of acid halide and compound (6) is normally carried out in a solvent. Said solvent is exemplified by halogenated hydrocarbons such as chloroform, dichloromethane and 1,1,2,2-tetrachloroethane, ethers such as diethyl ether, dioxane and tetrahydrofuran, acetone, acetonitrile, ethyl acetate and N,N-dimethylformamide. Also, the reaction may be carried out using an excess amount of compound (6) as a solvent. This reaction can be carried out in the presence or absence of a base. Said base is exemplified by organic bases such as trimethylamine, triethylamine, pyridine and N,N-dimethylaniline, and inorganic bases such as sodium hydrogen carbonate and potassium carbonate. Although the amount of compound (6) used is preferably about 1 to 2 mol equivalents per mol equivalent of acid halide, an excess amount of compound (6) may be used as a solvent. This reaction is normally carried out at about 0° C. to about +120° C. over a period of about 30 minutes to about 24 hours.

Compound (4) wherein Y is S can also be converted to compound (4) wherein Y is SO or $SO_2$ by a commonly known oxidation reaction. This reaction can be carried out by reacting compound (4) wherein Y is S with a peracid such as m-chloroperbenzoic acid or peracetic acid. This reaction is normally carried out in a solvent. Said solvent is exemplified by halogenated hydrocarbons such as dichloromethane, chloroform, carbon tetrachloride and 1,1,2,2-tetrachloroethane. By using a peracid at about 1 mol equivalent per mol equivalent of compound (4) wherein Y is S, compound (4) wherein Y is SO can be produced. This reaction is normally carried out at about −30° C. to about +10° C. over a period of about 30 minutes to about 24 hours. By using a peracid at about 2 mol equivalents per mol equivalent of compound (4) wherein Y is S, compound (4) wherein Y is $SO_2$ can be produced. This reaction is normally carried out at about 0° C. to about +50° C. over a period of about 30 minutes to about 24 hours.

Of the compounds represented by general formula (4), those wherein Q is an NH group can be isomerized as represented by general formulas (4-1) and (4-2), which isomers may be subjected to a reaction with a halogenated hydrocarbon represented by general formula (8) to yield compounds (9-1) and (9-2). This reaction is carried out in an appropriate solvent in the presence or absence of a base. Said solvent is exemplified by aromatic hydrocarbons such as benzene, toluene and xylene, ethers such as diethyl ether, tetrahydrofuran, dioxane and dimethoxyethane, N,N-dimethylformamide, dimethyl sulfoxide, acetonitrile and mixtures thereof. Said base is exemplified by bases selected as appropriate from alkali metal hydroxides such as sodium hydroxide and potassium hydroxide, alkaline earth metal hydroxides such as magnesium hydroxide and calcium hydroxide, alkali metal alkoxides such as sodium methoxide, sodium ethoxide and potassium tert-butoxide, alkali metal salts such as sodium carbonate, potassium carbonate, sodium hydrogen carbonate, potassium hydrogen carbonate, sodium acetate and potassium acetate, alkali metal hydrogen phosphates such as disodium hydrogen phosphate and dipotassium hydrogen phosphate, alkali metal hydrides such as sodium hydride and potassium hydride, and amines such as trimethylamine, triethylamine, pyridine, picoline, N-methylpyrrolidine, N-methylmorpholine and N,N-dimethylaniline. The amount of base used is preferably about 0 to about 5 mol equivalents per mol equivalent of compound (4); the amount of halogenated hydrocarbon (8) used is preferably about 1 to about 5 mol equivalents per mol equivalent of compound (4). This reaction is normally carried out at about 0° C. to about +180° C., preferably about +30° C. to +120° C., over a period of about 30 minutes to about 50 hours. Compounds (9-1) and (9-2) thus obtained may each be isolated and purified by known means of separation and purification such as concentration, concentration under reduced pressure, solvent extraction, crystallization, recrystallization, redissolution and chromatography.

Method B

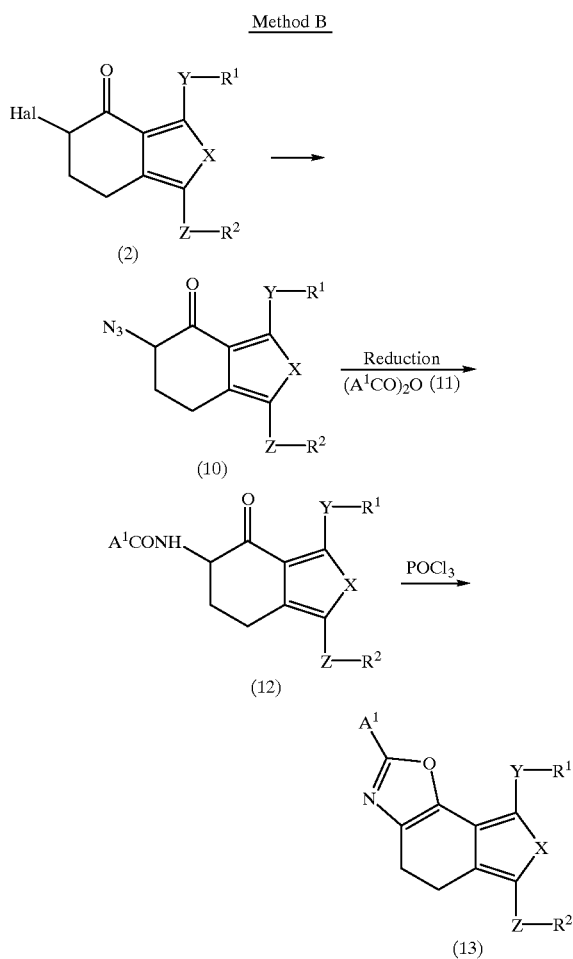

(In the above formulas, the symbols have the same definitions as those shown above.)

In this method, compound (12) is produced by azidating a compound represented by general formula (2) above by a commonly known method to yield compound (10), which is then reduced in the presence of a great excess of lower carboxylic anhydride (11) (e.g., acetic anhydride, propionic anhydride, butyric anhydride, isobutyric anhydride). Said reduction reaction is preferably catalytic reduction using a transition metal catalyst (e.g., palladium, platinum, rhodium) and hydrogen. Also, this reaction is carried out in a solvent that does not adversely affect the reaction. Said solvent is exemplified by aromatic hydrocarbons such as benzene, toluene and xylene, ethers such as diethyl ether, tetrahydrofuran, dioxane and dimethoxyethane, N,N-dimethylformamide, ethyl acetate, lower carboxylic acids corresponding to acid anhydride (11) (e.g., acetic acid, propionic acid, butyric acid, isobutyric acid) and mixtures thereof. Reaction temperature is normally about −20° C. to about +150° C., preferably about 0° C. to about +100° C., reaction time being about 1 hour to about 24 hours. Compound (12) thus obtained may be isolated and purified by known means of separation and purification such as concentration, concentration under reduced pressure, solvent extraction, crystallization, recrystallization, redissolution and chromatography.

By subjecting compound (12) to a reaction with phosphorus oxychloride in an appropriate solvent or in the absence of a solvent, compound (13) is produced. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane, dimethyl sulfoxide, acetonitrile and mixtures thereof. The amount of phosphorus oxychloride used is preferably about 1 to about 5 mol equivalents per mol equivalent of compound (12). Reaction temperature is normally about 0° C. to about +150° C., preferably about +30° C. to about +120° C., reaction time being about 1 hour to about 24 hours. Compound (13) thus obtained may be isolated and purified by known means of separation and purification such as concentration, concentration under reduced pressure, solvent extraction, crystallization, recrystallization, redissolution and chromatography.

By subjecting compound (13) wherein $R^2$ is —$COOR^6$ to a commonly known acid or alkali hydrolysis reaction, compound (13) wherein $R^2$ is —COOH can be produced. Also, by subjecting compound (13) wherein $R^2$ is —COOH to a commonly known amidation reaction [reaction with compound (6)], compound (13) wherein $R^2$ is —$CONR^4R^5$ can be produced. This reaction can be carried out under the same conditions as those for the reaction of compound (4') to compound (5) and the reaction of compound (5) to compound (7).

Compound (13) wherein Y is S can also be converted to compound (13) wherein Y is SO or $SO_2$ by a commonly known oxidation reaction. This reaction can be carried out under the same conditions as those for the reaction of compound (4) wherein Y is S to compound (4) wherein Y is SO or $SO_2$.

Method C

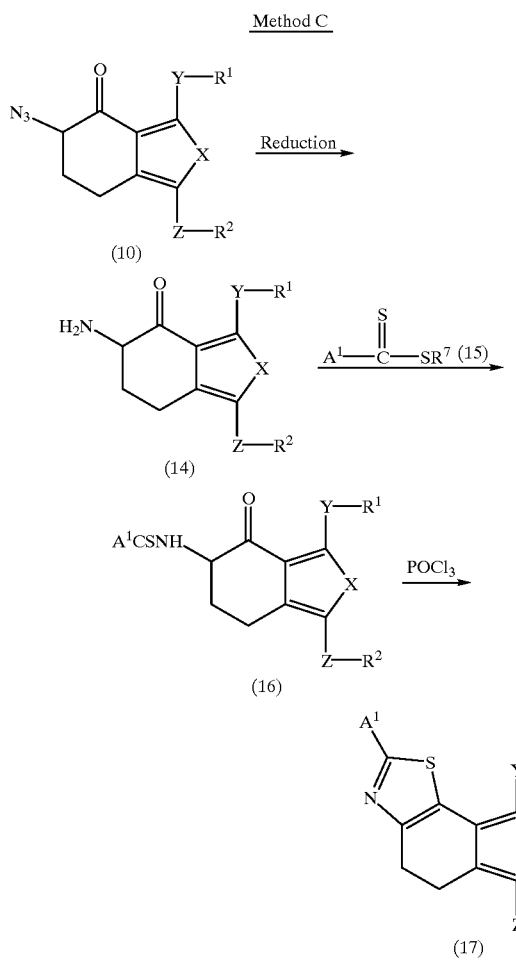

(In the above formulas, $R^7$ represents a methyl group or an ethyl group; the other symbols have the same definitions as those shown above.)

In this method, compound (14) is produced by reducing a compound represented by general formula (10) above. Said reduction reaction is preferably catalytic reduction using a transition metal catalyst (e.g., palladium, platinum, rhodium) and hydrogen. Also, this reaction is carried out in a solvent that does not adversely affect the reaction. Said solvent is exemplified by aromatic hydrocarbons such as benzene, toluene and xylene, ethers such as diethyl ether, tetrahydrofuran, dioxane and dimethoxyethane, alcohols such as methanol, ethanol, propanol, isopropanol, butanol, 2-methoxyethanol and ethylene glycol, N,N-dimethylformamide, ethyl acetate and mixtures thereof. Reaction temperature is normally about −20° C. to about +150° C., preferably about 0° C. to about +100° C., reaction time being about 1 hour to about 24 hours. Compound (14) thus obtained may be isolated and purified by known means of separation and purification such as concentration, concentration under reduced pressure, solvent extraction, crystallization, recrystallization, redissolution and chromatography.

By subjecting compound (14) to a reaction with a dithio ester represented by general formula (15) in an appropriate solvent or in the absence of a solvent, compound (16) is produced. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane, N,N-dimethylformamide, dimethyl sulfoxide, acetonitrile and mixtures thereof. The amount of dithio ester (15) used is preferably about 1 to about 5 mol equivalents per mol equivalent of compound (14). Reaction temperature is normally about 0° C. to about +150° C., preferably about +30° C. to about +120° C., reaction time being about 1 hour to about 24 hours. Compound (16) thus obtained may be isolated and purified by known means of separation and purification such as concentration, concentration under reduced pressure, solvent extraction, crystallization, recrystallization, redissolution and chromatography.

By reacting compound (16) with phosphorus oxychloride in the same manner as method B, compound (17) is produced.

By subjecting compound (17) wherein $R^2$ is —$COOR^6$ to a commonly known acid or alkali hydrolysis reaction, compound (17) wherein $R^2$ is —COOH can be produced. Also, by subjecting compound (17) wherein $R^2$ is —COOH to a commonly known amidation reaction [reaction with compound (6)], compound (17) wherein $R^2$ is —$CONR^4R^5$ can be produced. This reaction can be carried out under the same conditions as those for the reaction of compound (4') to compound (5) and the reaction of compound (5) to compound (7).

Compound (17) wherein Y is S can also be converted to compound (17) wherein Y is SO or $SO_2$ by a commonly known oxidation reaction. This reaction can be carried out under the same conditions as those for the reaction of compound (4) wherein Y is S to compound (4) wherein Y is SO or $SO_2$.

Method D

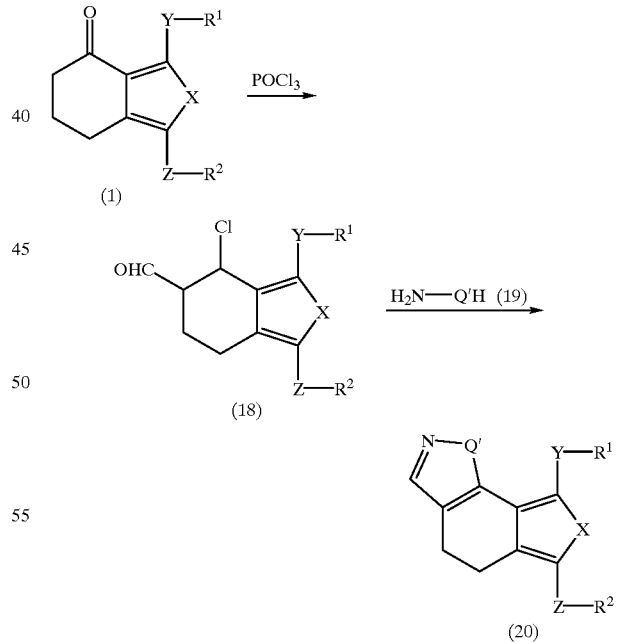

(In the above formulas, Q' represents an oxygen atom or $NA^1$; the other symbols have the same definitions as those shown above.)

In this method, compound (18) is produced by subjecting a compound represented by general formula (1) above to a reaction with phosphorus oxychloride in N,N- dimethylformamide. Useful solvents include, for example, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane and mixtures thereof. The amount of phosphorus oxychloride used is preferably about 1 to about 5 mol equivalents per mol equivalent of compound (1). Reaction temperature is normally about −20° C. to about +180° C., preferably about 0° C. to about +120° C., reaction time being about 1 hour to about 24 hours. Compound (18) thus obtained may be isolated and purified by known means of separation and purification such as concentration, concentration under reduced pressure, solvent extraction, crystallization, recrystallization, redissolution and chromatography.

Compound (20) is produced by a reaction of compound (18) and a hydroxylamine or hydrazine represented by general formula (19). This reaction is advantageously carried out in a solvent that does not adversely affect the reaction in the presence of a base. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane, N,N-dimethylformamide, dimethyl sulfoxide, acetonitrile and mixtures thereof. Said base is exemplified by bases selected as appropriate from alkali metal hydroxides such as sodium hydroxide and potassium hydroxide, alkaline earth metal hydroxides such as magnesium hydroxide and calcium hydroxide, alkali metal alkoxides such as sodium methoxide, sodium ethoxide and potassium tert-butoxide, alkali metal salts such as sodium carbonate, potassium carbonate, sodium hydrogen carbonate, potassium hydrogen carbonate, sodium acetate and potassium acetate, alkali metal hydrogen phosphates such as disodium hydrogen phosphate and dipotassium hydrogen phosphate, alkali metal hydrides such as sodium hydride and potassium hydride, and amines such as trimethylamine, triethylamine, pyridine, picoline, N-methylpyrrolidine, N-methylmorpholine and N,N-dimethylaniline. The amount of base used is preferably about 1 to about 5 mol equivalents per mol equivalent of compound (18); the amount of hydroxylamine or hydrazine (19) used is preferably about 1 to about 5 mol equivalents per mol equivalent of compound (18). This reaction is normally carried out at about 0° C. to about +180° C., preferably about +30° C. to about +120° C., over a period of about 30 minutes to about 50 hours. Compound (20) thus obtained may be isolated and purified by known means of separation and purification such as concentration, concentration under reduced pressure, solvent extraction, crystallization, recrystallization, redissolution and chromatography.

By subjecting compound (20) wherein $R^2$ is —$COOR^8$ to a commonly known acid or alkali hydrolysis reaction, compound (20) wherein $R^2$ is —COOH can be produced. Also, by subjecting compound (20) wherein $R^2$ is —COOH to a commonly known amidation reaction [reaction with compound (6)], compound (20) wherein $R^2$ is —$CONR^4R^5$ can be produced. This reaction can be carried out under the same conditions as those for the reaction of compound (4') to compound (5) and the reaction of compound (5) to compound (7).

Compound (20) wherein Y is S can also be converted to compound (20) wherein Y is SO or $SO_2$ by a commonly known oxidation reaction. This reaction can be carried out under the same conditions as those for the reaction of compound (4) wherein Y is S to compound (4) wherein Y is SO or $SO_2$.

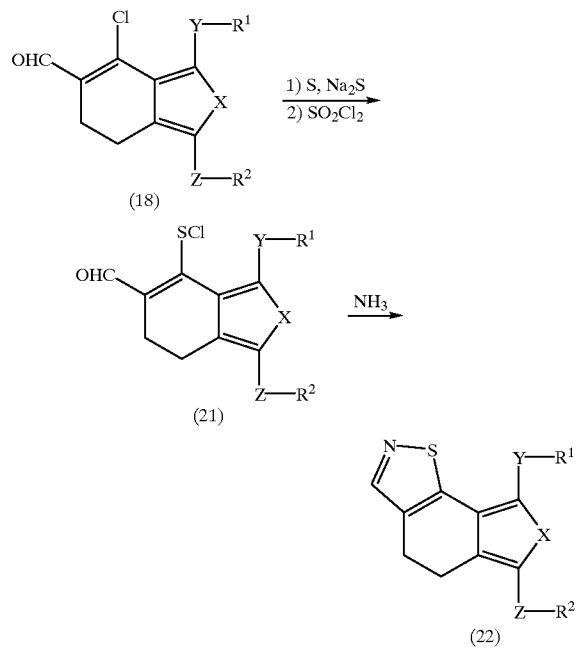

(In the above formulas, the symbols have the same definitions as those shown above.)

In this method, compound (21) is produced by subjecting a compound represented by general formula (18) above to a reaction with sulfur and sodium sulfide in an appropriate solvent and subsequently treating it with sulfuryl chloride. Said solvent is exemplified by ethers such as diethyl ether, tetrahydrofuran, dioxane and dimethoxyethane, alcohols such as methanol, ethanol, propanol, isopropanol, butanol, 2-methoxyethanol and ethylene glycol, N,N-dimethylformamide, dimethyl sulfoxide, acetonitrile and mixtures thereof. The amounts of sulfur and sodium sulfide used are each preferably about 1 to about 3 mol equivalents per mol equivalent of compound (18). Reaction temperature is normally about 0° C. to about +180° C., preferably about +30° C. to about +120° C., reaction time being about 1 hour to about 24 hours. The sulfuryl chloride treatment of the intermediate thus obtained is carried out in a solvent that does not adversely affect the reaction. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane and mixtures thereof. The amount of sulfuryl chloride used is preferably about 1 to about 3 mol equivalents per mol equivalent of compound (18). Reaction temperature is normally about −20° C. to about +150° C., preferably about 0° C. to about +100° C., reaction time being about 1 hour to about 24 hours. Compound (21) thus obtained may be isolated and purified by known means of separation and purification such as concentration, concentration under reduced pressure, solvent extraction, crystallization, recrystallization, redissolution and chromatography.

Compound (22) is produced by a reaction of compound (21) and a great excess of ammonia. This reaction is carried out in a solvent that does not adversely affect the reaction.

Said solvent is exemplified by ethers such as diethyl ether, tetrahydrofuran, dioxane and dimethoxyethane, alcohols such as methanol, ethanol, propanol, isopropanol, butanol, 2-methoxyethanol and ethylene glycol and mixtures thereof. This reaction is normally carried out at about −20° C. to about +180° C., preferably about 0° C. to about +120° C., over a period of about 1 hour to about 50 hours. Compound (22) thus obtained may be isolated and purified by known means of separation and purification such as concentration, concentration under reduced pressure, solvent extraction, crystallization, recrystallization, redissolution and chromatography.

By subjecting compound (22) wherein $R^2$ is —$COOR^6$ to a commonly known acid or alkali hydrolysis reaction, compound (22) wherein $R^2$ is —COOH can be produced. Also, by subjecting compound (22) wherein $R^2$ is —COOH to a commonly known amidation reaction [reaction with compound (6)], compound (22) wherein $R^2$ is —$CONR^4R^5$ can be produced. This reaction can be carried out under the same conditions as those for the reaction of compound (4') to compound (5) and the reaction of compound (5) to compound (7).

Compound (22) wherein Y is S can also be converted to compound (22) wherein Y is SO or $SO_2$ by a commonly known oxidation reaction. This reaction can be carried out under the same conditions as those for the reaction of compound (4) wherein Y is S to compound (4) wherein Y is SO or $SO_2$.

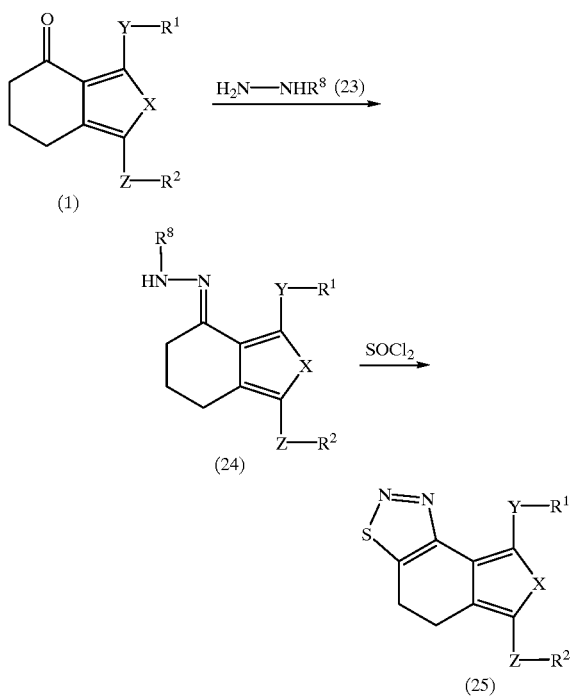

(In the above formulas, $R^8$ represents an ethoxycarbonyl group or a p-toluenesulfonyl group; the other symbols have the same definitions as those shown above.)

In this method, compound (24) is produced by subjecting a compound represented by general formula (1) above to a reaction with ethyl carbazinate or p-toluenesulfonyl hydrazide represented by general formula (23) in an appropriate solvent. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane, alcohols such as methanol, ethanol, propanol, isopropanol, butanol, 2-methoxyethanol and ethylene glycol, N,N-dimethylformamide, dimethyl sulfoxide, acetonitrile, ethyl acetate and mixtures thereof. The amount of ethyl carbazinate or p-toluenesulfonyl hydrazide (23) used is preferably about 1 to about 2 mol equivalents per mol -equivalent of compound (1). Reaction temperature is normally about 0° C. to about +180° C., preferably about +30° C. to about +120° C., reaction time being about 1 hour to about 24 hours. Compound (24) thus obtained may be isolated and purified by known means of separation and purification such as concentration, concentration under reduced pressure, solvent extraction, crystallization, recrystallization, redissolution and chromatography.

Compound (25) is produced by treating compound (24) with thionyl chloride. This reaction is carried out in an appropriate solvent or in the absence of a solvent. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane and mixtures thereof. This reaction is normally carried out at about −20° C. to about +180° C., preferably about 0° C. to about +120° C., over a period of about 1 hour to about 50 hours. Compound (25) thus obtained may be isolated and purified by known means or separation and purification such as concentration, concentration under reduced pressure, solvent extraction, crystallization, recrystallization, redissolution and chromatography.

By subjecting compound (25) wherein $R^2$ is —$COOR^6$ to a commonly known acid or alkali hydrolysis reaction, compound (25) wherein $R^2$ is —COOH can be produced. Also, by subjecting compound (25) wherein $R^2$ is —COOH to a commonly known amidation reaction [reaction with compound (6)], compound (25) wherein $R^2$ is —$CONR^4R^5$ can be produced. This reaction can be carried out under the same conditions as those for the reaction of compound (4') to compound (5) and the reaction of compound (5) to compound (7).

Compound (25) wherein Y is S can also be converted to compound (25) wherein Y is SO or $SO_2$ by a commonly known oxidation reaction. This reaction can be carried out under the same conditions as those for the reaction of compound (4) wherein Y is S to compound (4) wherein Y is SO or $SO_2$.

Method G

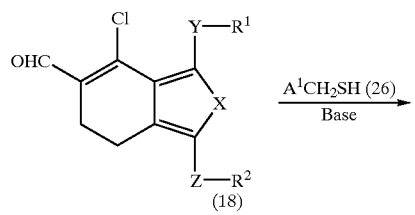

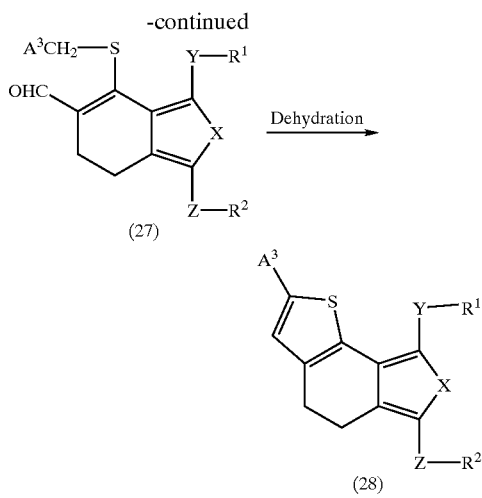

(In the above formulas, the symbols have the same definitions as those shown above.)

In this method, compound (27) is produced by subjecting a compound represented by general formula (18) above to a reaction with a thiol represented by general formula (26) in an appropriate solvent in the presence of a base. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane, N,N-dimethylformamide, dimethyl sulfoxide, acetonitrile, ethyl acetate and mixtures thereof. Said base is exemplified by bases selected as appropriate from alkali metal hydroxides such as sodium hydroxide and potassium hydroxide, alkaline earth metal hydroxides such as magnesium hydroxide and calcium hydroxide, alkali metal alkoxides such as sodium methoxide, sodium ethoxide and potassium tert-butoxide, alkali metal salts such as sodium carbonate, potassium carbonate, sodium hydrogen carbonate, potassium hydrogen carbonate, sodium acetate and potassium acetate, alkali metal hydrogen phosphates such as disodium hydrogen phosphate and dipotassium hydrogen phosphate, alkali metal hydrides such as sodium hydride and potassium hydride, and amines such as trimethylamine, triethylamine, pyridine, picoline, N-methylpyrrolidine, N-methylmorpholine and N,N-dimethylaniline. The amount of base used is preferably about 1 to about 5 mol equivalents per mol equivalent of compound (18); the amount of thiol (26) used is preferably about 1 to about 3 mol equivalents per mol equivalent of compound (18). This reaction is normally carried out at about 0° C. to about +180° C., preferably about +30° C. to about +120° C., over a period of about 1 hour to about 50 hours. Compound (27) thus obtained may be isolated and purified by known means of separation and purification such as concentration, concentration under reduced pressure, solvent extraction, crystallization, recrystallization, redissolution and chromatography.

Although compound (28) may be produced partially in the above reaction, it is normally produced by subjecting compound (27) to an aldol type dehydration condensation reaction. This reaction is carried out in a solvent that does not adversely affect the reaction. Said solvent is exemplified by aromatic hydrocarbons such as benzene, toluene and xylene, halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane, alcohols such as methanol, ethanol, propanol, isopropanol, butanol, 2-methoxyethanol and ethylene glycol, acetonitrile, ethyl acetate and mixtures thereof. Said dehydrating agent is selected as appropriate from lower carboxylic anhydrides such as acetic anhydride, propionic anhydride, butyric anhydride and isobutyric anhydride, sulfonic acids such as methanesulfonic acid and p-toluenesulfonic acid, and mixtures of amines (pyrrolidine, piperidine etc.) and carboxylic acids (acetic acid, benzoic acid etc.). The amount of dehydrating agent used is a catalytic amount to great excess, relative to compound (27); reaction temperature is normally about 0° C. to about +180° C., preferably about +30° C. to about +120° C., reaction time being about 1 hour to about 50 hours. Compound (28) thus obtained may be isolated and purified by known means of separation and purification such as concentration, concentration under reduced pressure, solvent extraction, crystallization, recrystallization, redissolution and chromatography.

By subjecting compound (28) wherein $R^2$ is —$COOR^6$ to a commonly known acid or alkali hydrolysis reaction, compound (28) wherein $R^2$ is —COOH can be produced. Also, by subjecting compound (28) wherein $R^2$ is —COOH to a commonly known amidation reaction [reaction with compound (6)], compound (28) wherein $R^2$ is —$CONR^4R^5$ can be produced. This reaction can be carried out under the same conditions as those for the reaction of compound (4') to compound (5) and the reaction of compound (5) to compound (7).

Compound (28) wherein Y is S can also be converted to compound (28) wherein Y is SO or $SO_2$ by a commonly known oxidation reaction. This reaction can be carried out under the same conditions as those for the reaction of compound (4) wherein Y is S to compound (4) wherein Y is SO or $SO_2$.

Method H

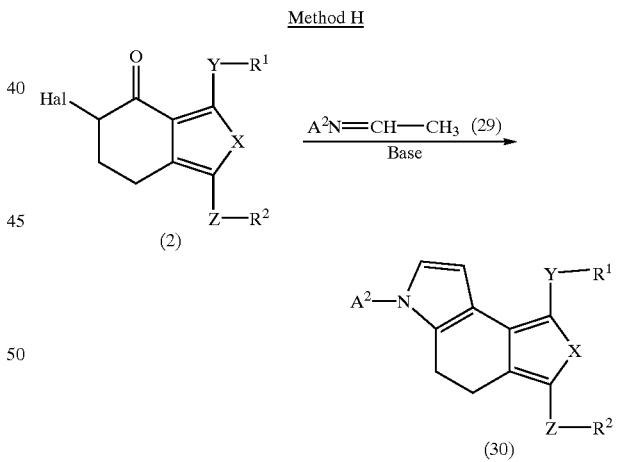

(In the above formulas, the symbols have the same definitions as those shown above.)

In this method, compound (30) is produced by subjecting a compound represented by general formula (2) above to a reaction with an imine represented by general formula (29) in an appropriate solvent in the presence of a base. Said solvent is exemplified by aromatic hydrocarbons such as benzene, toluene and xylene, ethers such as diethyl ether, tetrahydrofuran, dioxane and dimethoxyethane and mixtures thereof. Said base is exemplified by bases selected as appropriate from lithium diethylamide and lithium diisopropylamide. The amount of base used is preferably about 1 to about 2 mol equivalents per mol equivalent of compound (2); the amount of imine (29) used is preferably about 1 to about 2 mol equivalents per mol equivalent of compound (2). This reaction is advantageously carried out by first treating imine (29) with a base and subsequently adding compound (2). Reaction temperature is normally about −80° C. to about +100° C., preferably about −80° C. to about +30° C., reaction time being about 30 minutes to about 24 hours. Compound (30) thus obtained may be isolated and purified by known means of separation and purification such as concentration, concentration under reduced pressure, solvent extraction, crystallization, recrystallization, redissolution and chromatography.

By subjecting compound (30) wherein $R^2$ is —$COOR^6$ to a commonly known acid or alkali hydrolysis reaction, compound (30) wherein $R^2$ is —COOH can be produced. Also, by subjecting compound (30) wherein $R^2$ is —COOH to a commonly known amidation reaction (reaction with compound (6)], compound (30) wherein $R^2$ is —$CONR^4R^5$ can be produced. This reaction can be carried out under the same conditions as those for the reaction of compound (4') to compound (5) and the reaction of compound (5) to compound (7).

Compound (30) wherein Y is S can also be converted to compound (30) wherein Y is SO or $SO_2$ by a commonly known oxidation reaction. This reaction can be carried out under the same conditions as those for the reaction of compound (4) wherein Y is S to compound (4) wherein Y is SO or $SO_2$.

Regarding starting compound (1) for methods A through H, a compound known in the literature [Synthetic Communications, Vol. 25, p. 2,449 (1995); Journal of Medicinal Chemistry, Vol. 39, p. 398 (1996)] may be used as such, or it can be synthesized by the methods described therein or methods based thereof.

Of the compounds represented by general formula (1), those wherein X is a sulfur atom, for example, can be produced by method I below.

Method I

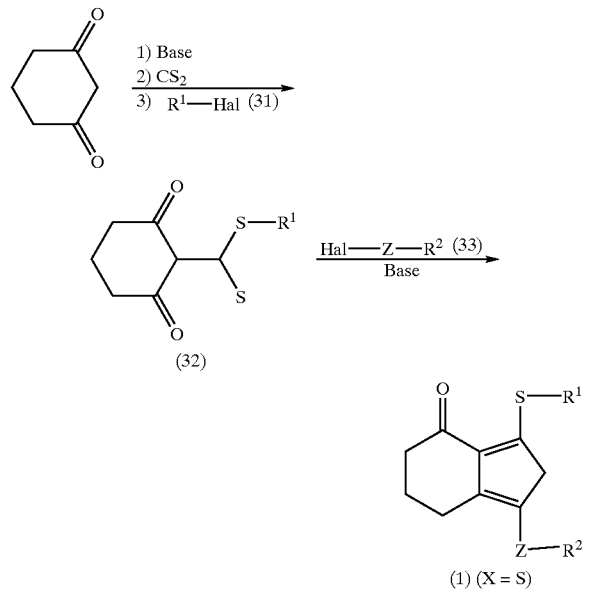

(In the above formulas, the symbols have the same definitions as those shown above.)

In this method, 1,3-cyclohexanedione is first treated with a base, carbon disulfide and halogenated hydrocarbon (31) in that order to yield a dithio ester represented by general formula (32). This reaction is carried out in a solvent that does not adversely affect the reaction. Said solvent is exemplified by aromatic hydrocarbons such as benzene, toluene and xylene, ethers such as diethyl ether, tetrahydrofuran, dioxane and dimethoxyethane, N,N-dimethylformamide, dimethyl sulfoxide, acetonitrile and mixtures thereof. Said base is exemplified by bases selected as appropriate from alkali metal hydroxides such as sodium hydroxide and potassium hydroxide, alkaline earth metal hydroxides such as magnesium hydroxide and calcium hydroxide, alkali metal alkoxides such as sodium methoxide, sodium ethoxide and potassium tert-butoxide, alkali metal salts such as sodium carbonate, potassium carbonate, sodium hydrogen carbonate, potassium hydrogen carbonate, sodium acetate and potassium acetate, alkali metal hydrogen phosphates such as disodium hydrogen phosphate and dipotassium hydrogen phosphate, alkali metal hydrides such as sodium hydride and potassium hydride, and amines such as trimethylamine, triethylamine, pyridine, picoline, N-methylpyrrolidine, N-methylmorpholine and N,N-dimethylaniline. The amount of base used is preferably about 1 to about 2 mol equivalents per mol equivalent of 1,3-cyclohexanedione; the amount of carbon disulfide used is preferably about 1 to about 2 mol equivalents per mol equivalent of 1,3-cyclohexanedione; the amount of halogenated hydrocarbon (31) used is preferably about 1 to about 2 mol equivalents, particularly about 1 mol equivalent, per mol equivalent of 1,3-cyclohexanedione. This reaction is normally carried out at about −80° C. to about +150° C., preferably about −20° C. to +100° C., over a period of about 1 hour to about 24 hours. Compound (32) thus obtained may be isolated and purified by known means of separation and purification such as concentration, concentration under reduced pressure, solvent extraction, crystallization, recrystallization, redissolution and chromatography.

Compound (1) is produced by subjecting compound (32) to a reaction with an ester represented by general formula (33) in an appropriate solvent in the presence of a base. Said solvent is exemplified by aromatic hydrocarbons such as benzene, toluene and xylene, ethers such as diethyl ether, tetrahydrofuran, dioxane and dimethoxyethane, alcohols such as methanol, ethanol, propanol, isopropanol, butanol, 2-methoxyethanol and ethylene glycol, ketones such as acetone and methyl ethyl ketone, N,N-dimethylformamide, dimethyl sulfoxide, acetonitrile, ethyl acetate and mixtures thereof. Said base is exemplified by bases selected as appropriate from alkali metal hydroxides such as sodium hydroxide and potassium hydroxide, alkaline earth metal hydroxides such as magnesium hydroxide and calcium hydroxide, alkali metal alkoxides such as sodium methoxide, sodium ethoxide and potassium tert-butoxide, alkali metal salts such as sodium carbonate, potassium carbonate, sodium hydrogen carbonate, potassium hydrogen carbonate, sodium acetate and potassium acetate, alkali metal hydrogen phosphates such as disodium hydrogen phosphate and dipotassium hydrogen phosphate, alkali metal hydrides such as sodium hydride and potassium hydride, and amines such as trimethylamine, triethylamine, pyridine, picoline, N-methylpyrrolidine, N-methylmorpholine and N,N-dimethylaniline. The amount of base used is preferably about 1 to about 10 mol equivalents, particularly about 1 to about 5 mol equivalents, per mol equivalent of compound (32); the amount of ester (33) used is preferably about 1 to about 2 mol equivalents per mol equivalent of compound (32). Reaction temperature is normally about 0° C. to about +180° C., preferably about +30° C. to about +120° C., reaction time being about 1 hour to about 24 hours. Compound (1) thus obtained may be isolated and purified by known means of separation and purification such as concentration, concentration under reduced pressure, solvent extraction, crystallization, recrystallization, redissolution and chromatography.

By subjecting compound (1) wherein $R^2$ is —$COOR^6$ to a commonly known acid or alkali hydrolysis reaction, compound (1) wherein $R^2$ is —COOH can be produced. Also, by subjecting compound (1) wherein $R^2$ is —COOH to a commonly known amidation reaction [reaction with compound (6)], compound (1) wherein $R^2$ is —$CONR^4R^5$ can be produced.

Compound (1) wherein Y is S can also be converted to compound (1) wherein Y is SO or $SO_2$ by a commonly known oxidation reaction. This reaction can be carried out under the same conditions as those for the reaction of compound (4) wherein Y is S to compound (4) wherein Y is SO or $SO_2$.

Of the compounds represented by general formula (1), those wherein X is an oxygen atom can be produced by method J below.

Method J

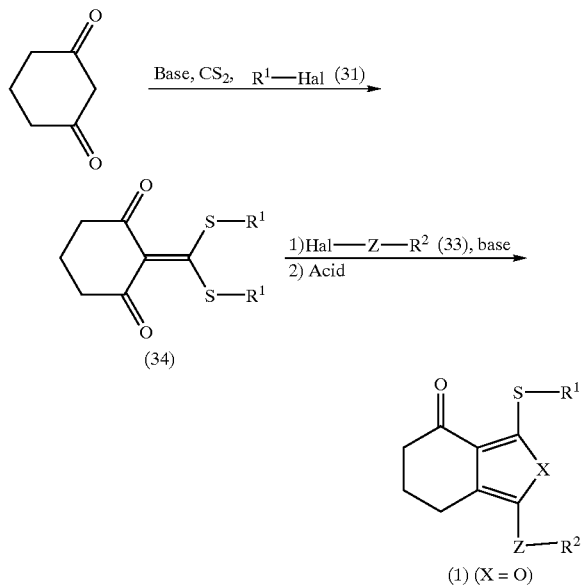

(In the above formulas, the symbols have the same definitions as those shown above.)

In this method, 1,3-cyclohexanedione is first treated with a base, carbon disulfide and halogenated hydrocarbon (31) in an appropriate solvent to yield a dithio acetal represented by general formula (34). Said solvent and base are selected as appropriate from the solvents and bases used to produce compound (32) by method I above. The amount of base used is preferably about 1 to about 5 mol equivalents, particularly about 2 to about 3 mol equivalents, per mol equivalent of 1,3-cyclohexanedione; the amount of carbon disulfide used is preferably about 1 to about 5 mol equivalents, particularly about 1 to about 2 mol equivalent, per mol equivalent of 1,3-cyclohexanedione; the amount of halogenated hydrocarbon (31) used is preferably about 2 to about 5 mol equivalents, particularly about 2 to about 3 mol equivalent, per mol equivalent of 1,3-cyclohexanedione. This reaction is normally carried out at about −80° C. to about +150° C., preferably about −20° C. to +100° C., over a period of about 1 hour to about 24 hours. Compound (34) thus obtained may be isolated and purified by known means of separation and purification such as concentration, concentration under reduced pressure, solvent extraction, crystallization, recrystallization, redissolution and chromatography.

Compound (1) is produced by subjecting compound (34) to a reaction with an ester represented by general formula (33) in an appropriate solvent in the presence of a base, and subsequently treating it with an acid. Said solvent is exemplified by aromatic hydrocarbons such as benzene, toluene and xylene, ethers such as diethyl ether, tetrahydrofuran, dioxane and dimethoxyethane and mixtures thereof. Said base is exemplified by bases selected as appropriate from lithium diisopropylamide, lithium bis(trimethylsilyl)amide, sodium bis(trimethylsilyl)amide and potassium bis (trimethylsilyl)amide. The amount of base used is preferably about 1 to about 2 mol equivalents per mol equivalent of compound (34); the amount of ester (33) used is preferably about 1 to about 2 mol equivalents per mol equivalent of compound (34). Reaction temperature is normally about −80° C. to about +100° C., preferably about −80° C. to about +50° C., reaction time being about 1 hour to about 24 hours. The acid treatment of the intermediate thus obtained is carried out in a solvent that does not adversely affect the reaction. When the acid used is an inorganic mineral acid such as hydrochloric acid, hydrobromic acid or sulfuric acid, useful solvents include ethers such as diethyl ether, tetrahydrofuran, dioxane and dimethoxyethane, alcohols such as methanol, ethanol, propanol, isopropanol, butanol, 2-methoxyethanol and ethylene glycol, ketones such as acetone and methyl ethyl ketone, acetonitrile, water and mixtures thereof. The amount of acid used is normally great excess. Reaction temperature is normally about 0° C. to about +150° C., preferably about +30° C. to about +100° C., reaction time being about 30 minutes to about 10 hours. When the acid used is a Lewis acid such as a boron trihalide (e.g., boron trichloride, boron trifluoride), an aluminum trihalide (e.g., aluminum chloride, aluminum bromide), a titanium tetrahalide (e.g., titanium tetrachloride, titanium tetrabromide) or a tin tetrahalide (e.g., tin tetrachloride, tin tetrabromide), useful solvents include halogenated hydrocarbons such as dichloromethane, chloroform, carbon tetrachloride, 1,2-dichloroethane and 1,1,2,2-tetrachloroethane, ethers such as diethyl ether, tetrahydrofuran, dioxane and dimethoxyethane and mixtures thereof. The amount of acid used is a catalytic amount to about 5 mol equivalents, preferably about 1 to about 2 mol equivalents, per mol equivalent of compound (34). Reaction temperature is normally about −30° C. to about +100° C., preferably about −10° C. to about +50° C., reaction time being about 30 minutes to about 10 hours. Compound (1) thus obtained may be isolated and purified by known means of separation and purification such as concentration, concentration under reduced pressure, solvent extraction, crystallization, recrystallization, redissolution and chromatography.

By subjecting compound (1) wherein $R^2$ is —$COOR^6$ to a commonly known acid or alkali hydrolysis reaction, compound (1) wherein $R^2$ is —COOH can be produced. Also, by subjecting compound (1) wherein $R^2$ is —COOH to a commonly known amidation reaction [reaction with compound (6)], compound (1) wherein $R^2$ is —$CONR^4R^5$ can be produced.

Compound (1) wherein Y is S can also be converted to compound (1) wherein Y is SO or $SO_2$ by a commonly known oxidation reaction. This reaction can be carried out under the same conditions as those for the reaction of compound (4) wherein Y is S to compound (4) wherein Y is SO or $SO_2$.

A compound represented by general formula (I) wherein ring A is an aromatic 5-membered heterocyclic ring that may be substituted for, and which is other than the above-mentioned ones, or a salt thereof, can also be produced in the same manner as the above-described methods.

Compound (I) or its salt as obtained by the above-described methods may be a hydrate or not.

The cell differentiation inducing factors serving as targets of the present invention include factors that induce a character of the process of differentiation of undifferentiated precursor cells that maintain living body function in particular tissue, such as osteoblasts and nerve cells, e.g., factors belonging to the TGF-β superfamily such as bone morphogenetic protein (BMP), neurotrophic factor, glial cell line-derived neurotropin factor (GDNF), tumor growth factor (TGF)-β and activin, factors belonging to the FGF superfamily such as basic fibroblast growth factor (bFGF): and acidic fibroblast growth factor (aFGF), factors belonging to the neuropoietic cytokine family such as leukocyte inhibition factor (LIF, or also called CDF) and ciliary neurotrophic factor (CNTF), interleukin (IL)-1, IL-2, IL-3, IL-5, IL-6, IL-7, IL-9, IL-11, tumor necrosis factor (TNF)-α and interferon (IFN)-γ, with preference given to BMP and neurotrophic factor. Examples of BMP include members of the BMP family of proteins that promote osteogenesis and chondrogenesis, such as BMP2, BMP4, BMP5, BMP6, BMP7, BMP8, BMP9, BMP10, BMP11 and BMP12, with preference given to BMP2, BMP4, BMP6 and BMP7. BMP may be a homo-dimer of each of the above-mentioned factors or a hetero-dimer consisting of any possible combination thereof. Neurotrophic factors include nerve growth factor (NGF), brain-derived neurotrophic factor (BDNF) and neurotrophine-3 (NT-3), with preference given to the NGF family. The cell differentiation induction factor action enhancer of the present invention, containing a compound represented by general formula (I) or a salt thereof, can be used to treat and prevent various bone diseases such as bone fractures and osteoporosis, and to treat and prevent nerve degeneration diseases in cerebral vascular dementia, senile dementia, Alzheimer's disease, etc., amyotrophic lateral sclerosis (Lou Gehrig disease) and various diseases based on cerebratl dysfunction or nerve degeneration such as depression and diabetic peripheral neuropathy. In addition, the compound of the present invention, represented by general formula (I), or a salt thereof, is expected to serve as a therapeutic drug and prophylactic drug for diseases wherein the pathologic condition is improved by enhancement of these actions by BMP, neurotrophic factor, etc., in addition to the above-described roles thereof in vivo. Also, the compound of the present invention, represented by general formula (I), or a salt thereof, possesses anti-matrix metalloprotease activity; including anti-collagenase activity, and can be used to treat and prevent osteoarthritis. Varying depending on patient condition and body weight and method of administration, the daily dose of the compound of the present invention, represented by general formula (I), or a salt thereof, is normally about 5 to about 1,000 mg, preferably about 10 to about 600 mg, and more preferably about 15 to about 150 mg, per day, based on the active ingredient [compound of the present invention, represented by general formula (I), or a salt thereof], per adult (weight 50 kg), administered in 1 to 3 portions per day. The compound represented by general formula (I) or a salt thereof is of low toxicity.

The compound of the present invention, represented by general formula (I), or a salt thereof, can be mixed in a carrier for bone reconstruction as an osteogenesis promoter in bone repair and bone transplantation because it possesses potent osteogenesis-promoting activity. For example, the compound represented by general formula (I) or a salt thereof can be used as adhered to, or contained in, artificial bones etc. prepared from metals, ceramics or high-molecular substances. The artificial bone is preferably made porous on the surface thereof to allow the effective release of the compound of the present invention, represented by general formula (I), or a salt thereof, in the living tissue upon its transplantation to a bone defect. The compound of the present invention, represented by general formula (I), or a salt thereof, can be adhered to, or contained in, an artificial bone by dispersing it in, an appropriate dispersant, binder, diluent or the like (e.g., collagen, physiological saline, citric acid solution, acetic acid solution, hydroxyapatite, fibrin, mixture thereof) and applying it to, or impregnating it in, the artificial bone. Such artificial bone is transplanted to a bone defect and firmly fixed to the defect. An artificial bone fixative can be prepared by mixing the active ingredient [compound represented by general formula (I) or a salt thereof] with pharmaceutically acceptable dispersants, binders, diluents, other components effective on bone regeneration. (e.g., calcium), etc. The artificial bone fixative can also be used as filled in the gap between the artificial bone transplanted to the bone defect in the host and the bone defect, without adhering it to, or containing it in, the artificial bone. It should also be noted that the non-oral composition described here can also be used with an osteogenesis-promoting protein such as the BMP family adhered thereto or contained therein.

The compound of the present invention, represented by general formula (I), or a salt thereof, possesses potent activity of enhancing cell differentiation inducing factor action and anti-matrix metalloprotease activity, and can be advantageously used in the treatment and prevention of various metabolic bone diseases such as osteoporosis, bone fractures, diseases based on nerve degeneration, and diseases such as osteoarthritis, rheumatoid arthritis, arteriosclerosis and cancer metastasis, in mammals (e.g., humans, mice, rats, rabbits, cats, dogs, bovines, pigs).

BEST MODE FOR CARRYING OUT THE INVENTION

Figure 1A:
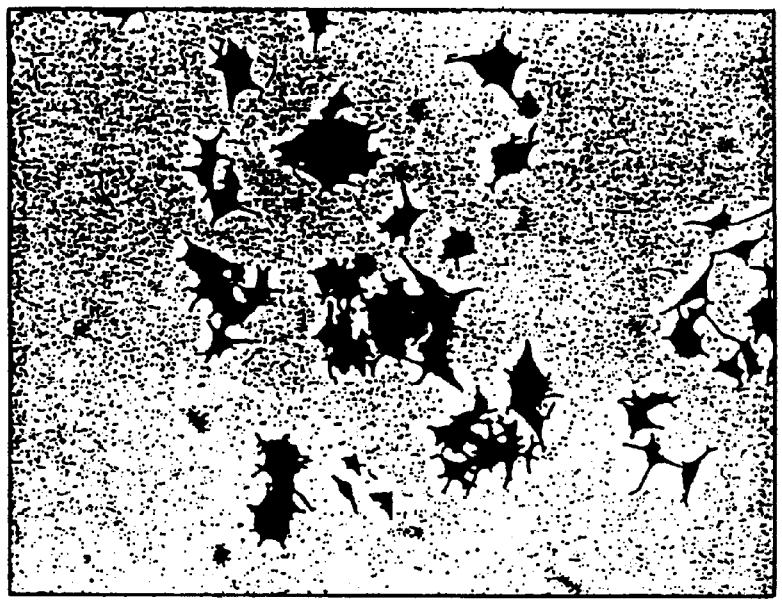
FIG. 1 shows the activity of enhancing neurite out-growth in a rat pheochromocytoma.

The present invention is hereinafter described in more detail by means of the following test examples, reference examples, working examples and preparation examples, which are not to be construed as limitative.

In the test examples, reference examples, working examples and preparation example below, "room temperature" means about +15° C. to about +25° C.

EXAMPLES

Test Example 1

Osteogenesis-promoting Action

Using stromal cells prepared from the femoral marrow of a normal rat, alkaline phosphatase activity was determined as an index of osteogenesis. Specifically, stromal cells, prepared from the femoral marrow of a 7-week-old male Sprague-Dawley rat by the method of Maniatopoulos et al. [Cell Tissue Research, Vol. 254, p. 317 (1988)], were cultured in an α-MEM (minimum-essential medium) solution containing both dexamethasone ($10^{-7}$ M) and β-glycerophosphoric acid ($10^{-2}$ M) to obtain calcified osteoid tissue. One week later, the test compound ($10^{-7}$ M or $10^{-5}$ M) was added to the confluent cells, followed by 10 to 14 more days of cultivation in the above culture medium. After washing with phosphate buffer, the cells were homogenized with 0.2% Nonidet P-40 and centrifuged at 3,000 rpm for 10 minutes. The resulting supernatant was assayed for alkaline phosphatase activity by the method of Lowry et al. [Journal of Biological Chemistry, Vol. 207, p. 19 (1954)]. The values obtained are given in mean±SE in Table 1. The data were statistically analyzed by Student's t-test.

TABLE 1

| Compound (Example No.) | Concentration (M) | Alkaline Phosphatase Activity (nmol p-nitrophenol/min/well) |
|---|---|---|
| (1) Experiment 1 | | |
| Control | Not added | 694.9 ± 22.7 |
| 46 | $10^{-5}$ | 1,916.8 ± 26.3** |
| (2) Experiment 2 | | |
| Control | Not added | 608.4 ± 20.9 |
| 50 | $10^{-5}$ | 1,463.9 ± 33.4** |
| (3) Experiment 3 | | |
| Control | Not added | 63.1 ± 5.0 |
| 90 | $10^{-6}$ | 102.9 ± 7.3** |
| 91 | $10^{-6}$ | 123.2 ± 5.7** |
| 92 | $10^{-6}$ | 111.4 ± 2.1** |
| 93 | $10^{-6}$ | 159.9 ± 17.5** |

**, $p < 0.01$ vs control

Test Example 2
Alkaline Phosphatase Production Induction Capability in Mouse Osteoblast Strain Mouse-derived osteoblast strain $MC_3T3$-E1 in α-MEM containing 10% fetal calf serum (FCS) was seeded to 96-well plates (8,000 cells/well); two days later, the sample, previously diluted with a medium containing or not containing 3 ng/ml BMP-4/7 of heterodimer (described in EP-A-0626451) to each concentration shown in Table 2, was added to the cells reaching a confluent state, followed by cultivation for 72 hours. After each plate was once washed with saline, substrate solution was added, followed by incubation at room temperature for 15 minutes. The reaction was stopped by 0.05 N sodium hydroxide, and the absorbance at 405 nm was determined. The values obtained are given in mean±S.E. in Table 2. The data were statistically analyzed by Student's t-test.

TABLE 2

| Compound (Example No.) | Concentration (M) | Alkaline Phosphatase Activity ($A_{405} \times 1,000$) | |
|---|---|---|---|
| | | BMP Added (3 ng/ml) | BMP Not Added |
| (1) Experiment 4 | | | |
| Control | Not added | 397 ± 30 | 135 ± 2 |
| 36 | $10^{-5}$ | 618 ± 13* | 181 ± 6* |
| (2) Experiment 5 | | | |
| Control | Not added | 420 ± 1 | 141 ± 8 |
| 47 | $10^{-5}$ | 886 ± 35* | 202 ± 21* |

*, $p < 0.05$ vs control

Figure 1B:

Test Example 3
Activity of Enhancing Neurite Out-growth in a Rat Pheochromocytoma $PC_{12}$ cells (rat pheochromocytoma, 2,000 cells/well) in suspension in Dulbecco's MEM supplemented with 10% FCS were mixed with NGF (5 ng/ml) at the concentration shown in FIG. 1 and the compound of Example 37 (10 μM) and seeded to 96-well plates, followed by cultivation for 3 days. After the culture medium was removed, hematoxylin/eosine staining was conducted using a commercial kit (Difquick R, Kokusai Shiyaku). The results of microscopic evaluation of neurite out-growth are shown in FIG. 1.

Test Example 4
Anti-collagenase Action in Rabbit Chondrocytes

Chondrocytes, prepared from rabbit rib cartilage, were suspended in Dulbecco's MEM (DMEM) supplemented with 10% FCS, sown to 12-well plates, and cultured until a confluent state was reached. After the culture broth was-removed, the cells were cultured for 48 hours in serum-free DMEM containing IL-1 (30 ng/ml) and the sample compound. The collagenase produced upon induction by IL-1 stimulation and secreted in the culture broth was activated by trypsinization; after a soybean trypsin inhibitor was added to inactivate the trypsin, activity was determined with type I collagen as the substrate. The values obtained are given in mean±SE in Table 3. The data were statistically analyzed by Student's t-test.

TABLE 3

| | Experiment 6 | | |
|---|---|---|---|
| IL-1 (30 ng/ml) | Compound (Example No.) | Concentration (M) | Collagenase Activity (units/ml) |
| Not added | Control | Not added | 0.1 ± 0.1 |
| Added | Control | Not added | 21.9 ± 1.7 |
| Added | 25 | $10^{-6}$ | 11.0 ± 0.8* |
| Added | 25 | $10^{-5}$ | 1.8 ± 0.6** |

*$p < 0.05$;
**$p < 0.01$ vs control (IL-1, 30 ng/ml)

Reference Example 1

Sodium hydride (60% suspension in oil, 10.15 g) was suspended in N,N-dimethylformamide (DMF) (90 ml) and cooled to −10° C.; a solution of 1,3-cyclohexanedione (20.33 g) in DMF (90 ml) was added dropwise over a period of 40 minutes. After this mixture was stirred at −10° C. for 30 minutes, a solution of carbon disulfide (19.33 g) in DMF (30 ml) was added dropwise at −10° C. over a period of 15 minutes, followed by stirring at room temperature for 10 minutes and at 50° C. for 1.5 hours. After the mixture was again cooled to −10° C., a solution of iodomethane (25.74 g) in DMF (70 ml) was added dropwise over a period of 30 minutes, followed by stirring at room temperature for 15 hours. The precipitate was filtered off; the filtrate was concentrated under reduced pressure and diluted with 0.5 N hydrochloric acid (500 ml), after which it was extracted with ethyl acetate. The organic layer was washed with water and dried ($MgSO_4$), after which the solvent was distilled off. The residue was subjected to silica gel column chromatography and eluted with ethyl acetate-hexane (1:6, v/v) to yield methyl 1,3-dioxocyclohexane-2-dithiocarboxylate (9.68 g, 26.4%). Orange oily substance. NMR (δ ppm in $CDCl_3$): 2.00 (2H, quintet, J=7 Hz), 2.57 (3H, s), 2.60 (2H, t, J=6 Hz), 2.80 (2H, t, J=6 Hz).

Reference Example 2

To a mixture of ethyl 1,3-dioxocyclohexane-2-dithiocarboxylate (1.68 g), ethyl 4-bromochrotonate (1.92 g) and acetone (40 ml), potassium carbonate (5.74 g) was added at room temperature, followed by refluxing under heating for 3 hours. The reaction mixture was poured over water (300 ml) and extracted with ethyl acetate. The organic layer was washed with water and dried ($MgSO_4$), after which the solvent was distilled off. The residue was subjected to silica gel column chromatography and eluted with ethyl acetate-hexane (1:6 to 1:3, v/v) to yield ethyl (E)-3-[4,5,6,7-tetrahydro-3-methylthio-4-oxo-1-benzo[c]thienyl] acrylate (1.20 g, 48.8%), which was then recrystallized from ethyl acetate-hexane. Yellow prisms crystal. Melting point 104–105° C.

Reference Example 3

1,3-Cyclohexanedione (50.90 g) was dissolved in N,N-dimethylformamide (400 ml); potassium carbonate (188.22 g) and carbon disulfide (51.85 g) were added at room temperature. Iodomethane (173.97 g) was then added dropwise over a period of 1.5 hours, followed by stirring at room temperature for 2 hours. The reaction mixture was poured over water (1,200 ml) and extracted with ethyl acetate. The organic layer was washed with water and dried ($MgSO_4$), after which the solvent was distilled off. The residue was subjected to silica gel column chromatography and eluted with ethyl acetate-hexane (1:1 to 2:1, v/v) to yield 2-[bis(methylthio)methylene]cyclohexane-1,3-dione (39.49 g, 40.2%), which was then recrystallized from ethyl acetate-hexane. Yellow prisms. Melting point 66–67° C.

Reference Example 4

Lithium bis(trimethylsilyl)amide (1.0 M hexane solution, 154.0 ml) was added dropwise to tetrahydrofuran (THF) (265 ml) at −78° C. in a nitrogen stream over a period of 25 minutes. A solution of ethyl bromoacetate (25.71 g) in THF (50 ml) was then added dropwise at −78° C. over a period of 15 minutes; a solution of 2-[bis(methylthio)methylene]cyclohexane-1,3-dione (25.62 g) in THF (240 ml) was further added drop by drop at −78° C. over a period of 30 minutes. After the reaction mixture was stirred at −78° C. for 1 hour and at room temperature for 15 hours, it was poured over an ice cooled saturated aqueous solution of ammonium chloride (1,250 ml) and stirred at room temperature for 15 minutes. The organic layer was separated; the aqueous layer was extracted with ethyl acetate. The organic layers were combined, washed with water and dried ($MgSO_4$), after which the solvent was distilled off. The residue was subjected to silica gel column chromatography and eluted with ethyl acetate-hexane (2:1, v/v) to yield an oily substance. The oily substance obtained was dissolved in diethyl ether (250 ml); a boron trifluoride-diethyl ether complex (25.21 g) was added at room temperature. After the reaction mixture was stirred at room temperature for 1 hour, it was poured over water (500 ml); the organic layer was separated; the aqueous layer was extracted with ethyl acetate. The organic layers were combined, washed with water and dried ($MgSO_4$), after which the solvent was distilled off. The residue was subjected to silica gel column chromatography and eluted with ethyl acetate-hexane (1:3, v/v) to yield ethyl 4,5,6,7-tetrahydro-3-methylthio-4-oxobenzo[c]furan-1-carboxylate (4.41 g, 14.6%), which was then recrystallized from ethyl acetate-hexane. Colorless plates. Melting point 123–124° C.

Reference Example 5

Ethyl 4,5,6,7-tetrahydro-3-methylthio-4-oxobenzo[c]thiophene-1-carboxylate (25.12 g) was dissolved in chloroform (400 ml); a solution of bromine (15.59 g) in chloroform (20 ml) was added dropwise at room temperature over a period of 30 minutes. After the reaction mixture was stirred at room temperature for 40 minutes, it was washed with a 2% aqueous solution of sodium sulfite (400 ml), water, a saturated aqueous solution of sodium hydrogen carbonate and water in that order, and dried ($MgSO_4$), after which the solvent was distilled off to yield ethyl 5-bromo-4,5,6,7-tetrahydro-3-methylthio-4-oxobenzo[c]thiophene-1-carboxylate (28.27 g, 87.1%), which was then recrystallized from ethyl acetate-hexane. Light-yellow prisms. Melting point 147–148° C.

Reference Example 6

Ethyl 4,5,6,7-tetrahydro-4-oxo-3-propylthiobenzo[c]thiophene-1-carboxylate (25.29 g) was dissolved in chloroform (380 ml); a solution of bromine (13.81 g) in chloroform (20 ml) was added dropwise at room temperature over a period of 20 minutes. After the reaction mixture was stirred at room temperature for 40 minutes, it was washed with a 2% aqueous solution of sodium sulfite (400 ml), water, a saturated aqueous solution of sodium hydrogen carbonate and water in that order, and dried ($MgSO_4$), after which the solvent was distilled off to yield ethyl 5-bromo-4,5,6,7-tetrahydro-4-oxo-3-propylthiobenzo[c]thiophene-1-carboxylate (29.07 g, 90.9%), which was then recrystallized from ethyl acetate-hexane. Light-yellow prisms. Melting point 93–94° C.

Reference Example 7

Ethyl 4,5,6,7-tetrahydro-3-isopropylthio-4-oxobenzo[c]thiophene-1-carboxylate (2.50 g) was dissolved in methanol (80 ml); a solution of bromine (1.34 g) in methanol (8.6 ml) was added dropwise at room temperature. After the reaction mixture was stirred at room temperature for 2 hours, it was poured over water and extracted with ethyl acetate. The organic layer was washed with an aqueous solution of sodium thiosulfate, a saturated aqueous solution of sodium hydrogen carbonate and water in that order, and dried ($MgSO_4$), after which the solvent was distilled off. The residue was subjected to silica gel column chromatography and eluted with ethyl acetate-hexane (1:5, v/v) to yield ethyl 5-bromo-4,5,6,7-tetrahydro-3-isopropylthio-4-oxobenzo[c]thiophene-1-carboxylate (2.65 g, 83.9%), which was then recrystallized from ethyl acetate-hexane. Colorless prisms. Melting point 107–108° C.

Reference Example 8

In the same manner as in Reference Example 5, ethyl 5-bromo-3-butylthio-4,5,6,7-tetrahydro-4-oxobenzo[c]thiophene-1-carboxylate was obtained from ethyl 3-butylthio-4,5,6,7-tetrahydro-4-oxobenzo[c]thiophene-1-carboxylate, which was then recrystallized from ethyl acetate-hexane. Colorless prisms. Melting point 81–82° C.

Reference Example 9

In the same manner as in Reference Example 5, ethyl 3-benzylthio-5-bromo-4,5,6,7-tetrahydro-4-oxobenzo[c]thiophene-1-carboxylate was obtained from ethyl 3-benzylthio-4,5,6,7-tetrahydro-4-oxobenzo[c]thiophene-1-carboxylate, which was then recrystallized from ethyl acetate-hexane. Colorless prisms. Melting point 131–132° C.

Reference Example 10

Ethyl 4,5,6,7-tetrahydro-3-methylthio-4-oxobenzo[c]furan-1-carboxylate (4.26 g) was dissolved in chloroform (75 ml); a solution of bromine (2.73 g) in chloroform (5 ml) was added dropwise at room temperature over a period of 10 minutes. After the reaction mixture was stirred at room temperature for 30 minutes, it was washed with a 2% aqueous solution of sodium sulfite (100 ml), water, a saturated aqueous solution of sodium hydrogen carbonate and water in that order, and dried (MgSO$_4$), after which the solvent was distilled off to yield ethyl 5-bromo-4,5,6,7-tetrahydro-3-methylthio-4-oxobenzo[c]furan-1-carboxylate (5.01 g, 89.8%), which was then recrystallized from ethyl acetate-hexane. Colorless needles. Melting point 130–131° C.

Reference Example 11

Ethyl 5-bromo-4,5,6,7-tetrahydro-3-methylthio-4-oxobenzo[c]thiophene-1-carboxylate (5.24 g) was suspended in N,N-dimethylformamide (80 ml); a solution of sodium azide (1.95 g) in water (12 ml) was added at 0° C. After the reaction mixture was stirred at room temperature for 4 hours, it was poured over water (50 ml) and extracted with ethyl acetate. The organic layer was washed with water and dried (MgSO$_4$), after which the solvent was distilled off. The residue was subjected to silica gel column chromatography and eluted with ethyl acetate-hexane (1:9 to 1:2, v/v) to yield ethyl 5-azido-4,5,6,7-tetrahydro-3-methylthio-4-oxobenzo[c]thiophene-1-carboxylate (3.77 g, 80.7%), which was then recrystallized from ethyl acetate-hexane. Colorless needles. Melting point 163–164° C. (decomposed).

Reference Example 12

Ethyl 5-bromo-4,5,6,7-tetrahydro-3-isopropylthio-4-oxobenzo[c]thiophene-1-carboxylate (2.55 g) was dissolved in N,N-dimethylformamide (30 ml); a solution of sodium azide (0.88 g) in water (5 ml) was added at 0° C. After the reaction mixture was stirred at room temperature for 50 minutes, it was poured over water and extracted with ethyl acetate. The organic layer was washed with water and dried (MgSO$_4$), after which the solvent was distilled off. The residue was subjected to silica gel column chromatography and eluted with ethyl acetate-hexane (1:9, v/v) to yield ethyl 5-azido-4,5,6,7-tetrahydro-3-isopropylthio-4-oxobenzo[c]thiophene-1-carboxylate (1.70 g, 74.2%), which was then recrystallized from ethyl acetate-hexane. Colorless prisms. Melting point 118–119° C.

Reference Example 13

In the same manner as in Reference Example 11, ethyl 5-azido-4,5,6,7-tetrahydro-4-oxo-3-propylthiobenzo[c]thiophene-1-carboxylate was obtained from ethyl 5-bromo-4,5,6,7-tetrahydro-4-oxo-3-propylthiobenzo[c]thiophene-1-carboxylate, which was then recrystallized from ethyl acetate-hexane. Colorless needles. Melting point 83–84° C.

Reference Example 14

In the same manner as in Reference Example 11, ethyl 5-azido-3-butylthio-4,5,6,7-tetrahydro-4-oxobenzo[c]thiophene-1-carboxylate was obtained from ethyl 5-bromo-3-butylthio-4,5,6,7-tetrahydro-4-oxobenzo[c]thiophene-1-carboxylate. Green oily substance. NMR (δ ppm in CDCl$_3$): 0.98 (3H, t, J=7 Hz), 1.38 (3H, t, J=7 Hz), 1.45–1.63 (2H, m), 1.74–1.89 (2H, m), 1.94–2.09 (1H, m), 2.22–2.31 (1H, m), 2.91–3.08 (1H, m), 3.05 (2H, t, J=7 Hz), 3.45–3.59 (1H, m), 4.18 (1H, dd, J=11 & 5 Hz), 4.33 (2H, q, J=7 Hz).

Reference Example 15

In the same manner as in Reference Example 11, ethyl 5-azido-4,5,6,7-tetrahydro-3-methylthio-4-oxobenzo[c]furan-1-carboxylate was obtained from ethyl 5-bromo-4,5,6,7-tetrahydro-3-methylthio-4-oxobenzo[c]furan-1-carboxylate, which was then recrystallized from ethyl acetate-hexane. Colorless needles. Melting point 131–132° C.

Example 1

A mixture of ethyl 5-bromo-4,5,6,7-tetrahydro-3-methylthio-4-oxobenzo[c]thiophene-1-carboxylate (2.09 g), thioacetamide (0.90 g) and ethanol (100 ml) was refluxed under heating for 7 hours, after which it was concentrated under reduced pressure, diluted with water (50 ml) and extracted with ethyl acetate. The organic layer was washed with water and dried (MgSO$_4$), after which the solvent was distilled off. The residue was subjected to silica gel column chromatography and eluted with ethyl acetate-hexane (1:19 to 1:9, v/v) to yield ethyl 4,5-dihydro-2-methyl-8-methylthiothieno[3,4-e]benzothiazole-6-carboxylate (0.86 g, 44%), which was then recrystallized from ethyl acetate-hexane. Yellow prisms. Melting point 143–144° C.

Example 2

A mixture of ethyl 5-bromo-4,5,6,7-tetrahydro-3-methylthio-4-oxobenzo[c]thiophene-1-carboxylate (6.99 g), thiobenzamide (5.49 g) and ethanol (150 ml) was refluxed under heating for 3 hours, after which it was poured over water (500 ml) and extracted with ethyl acetate-tetrahydrofuran (3:1, v/v). The organic layer was washed with water and dried (MgSO$_4$), after which the solvent was distilled off. The residue was subjected to silica gel column chromatography and eluted with chloroform-hexane (1:1, v/v) to yield ethyl 4,5-dihydro-8-methylthio-2-phenylthieno[3,4-e]benzothiazole-6-carboxylate (2.63 g, 33.9%), which was then recrystallized from ethyl acetate-hexane. Colorless needles. Melting point 153–154° C.

Example 3

A mixture of ethyl 5-bromo-4,5,6,7-tetrahydro-4-oxo-3-propylthiobenzo[c]thiophene-1-carboxylate (9.43 g), thiobenzamide (6.86 g) and ethanol (190 ml) was refluxed under heating for 4 hours, after which it was poured over water (600 ml) and extracted with ethyl acetate. The organic layer was washed with water and dried (MgSO$_4$), after which the solvent was distilled off. The residue was subjected to silica gel column chromatography and eluted with ethyl acetate-hexane (1:10, v/v) to yield ethyl 4,5-dihydro-2-phenyl-8-propylthiothieno[3,4-e]-benzothiazole-6-carboxylate (3.63 g, 34.9%), which was then recrystallized from ethyl acetate-hexane. Yellow prisms. Melting point 125–126° C.

Example 4

A mixture of ethyl 5-bromo-4,5,6,7-tetrahydro-3-methylthio-4-oxobenzo[c]furan-1-carboxylate (2.60 g), thiobenzamide (2.14 g) and ethanol (60 ml) was refluxed under heating for 5 hours, after which it was diluted with ethyl acetate-tetrahydrofuran (3:1, v/v, 400 ml), washed with water and dried (MgSO$_4$), after which the solvent was distilled off to yield ethyl 4,5-dihydro-8-methylthio-2-phenylfuro[3,4-e]benzothiazole-6-carboxylate (1.67 g, 57.6%), which was then recrystallized from ethyl acetate-hexane. Colorless needles. Melting point 170–171° C.

Examples 5 through 10

The compounds shown in Table 4 were obtained in the same manner as in Example 1.

TABLE 4

| Example No. | X | R¹ | A¹ | Recovery (%) | Melting Point (° C.) | Recrystallizing Solvent |
|---|---|---|---|---|---|---|
| 5 | S | CH₃ | C₂H₅ | 54 | 119–120 | Ethyl acetate-hexane |
| 6 | S | CH₃ | C₆H₅CH=CH (E) | 36 | 171–172 | Ethyl acetate-hexane |
| 7 | S | CH₃CH₂CH₂ | CH₃ | 53 | 87–88 | Ethyl acetate-hexane |
| 8 | S | C₆H₅CH₂ | CH₃ | 43 | 143–144 | Ethyl acetate-hexane |
| 9 | S | C₆H₅CH₂ | C₆H₅ | 39 | 155–156 | Ethyl acetate-hexane |
| 10 | O | CH₃ | CH₃ | 44 | 146–147 | Ethyl acetate-hexane |

Example 11

A mixture of ethyl 5-azido-4,5,6,7-tetrahydro-3-methylthio-4-oxobenzo[c]thiophene-1-carboxylate (3.62 g), palladium-carbon (5%, 50% wet, 4.0 g), acetic acid (70 ml) and acetic anhydride (35 ml) was subjected to a catalytic reduction reaction at room temperature under 1 atm. The insoluble substances were filtered off; the filtrate was concentrated under reduced pressure; the residue was dissolved in ethyl acetate-tetrahydrofuran (3:1, v/v). This solution was washed with water, a saturated aqueous solution of sodium hydrogen carbonate and water in that order, and dried (MgSO₄), after which the solvent was distilled off to yield ethyl 5-acetylamino-4,5,6,7-tetrahydro-3-methylthio-4-oxobenzo[c]thiophene-1-carboxylate (2.81 g, 73.8%), which was then recrystallized from chloroform-ethanol. Colorless needles. Melting point 215–216° C.

Example 12

A mixture of ethyl 5-azido-4,5,6,7-tetrahydro-3-isopropylthio-4-oxobenzo[c]thiophene-1-carboxylate (1.60 g), palladium-carbon (5%, 50% wet, 1.6 g), acetic acid (30 ml) and acetic anhydride (15 ml) was subjected to a catalytic reduction reaction at room temperature under 1 atm. The insoluble substances were filtered off; the filtrate was poured over water and extracted with ethyl acetate. The organic layer was washed with water, a saturated aqueous solution of sodium hydrogen carbonate and water in that order, and dried (MgSO₄), after which the solvent was distilled off to yield ethyl 5-acetylamino-4,5,6,7-tetrahydro-3-isopropylthio-4-oxobenzo[c]thiophene-1-carboxylate (1.30 g, 77.8%), which was then recrystallized from ethyl acetate-hexane. Colorless prisms. Melting point 170–171° C.

Example 13

A mixture of ethyl 5-azido-4,5,6,7-tetrahydro-4-oxo-3-propylthiobenzo[c]thiophene-1-carboxylate (4.24 g), palladium-carbon (5%, 50% wet, 4.0 g), propionic acid (70 ml) and propionic anhydride (35 ml) was subjected to a catalytic reduction reaction at room temperature under 1 atm. The insoluble substances were filtered off; the filtrate was concentrated under reduced pressure; the residue was dissolved in ethyl acetate-tetrahydrofuran (3:1, v/v). This solution was washed with water, a saturated aqueous solution of sodium hydrogen carbonate and water in that order, and dried (MgSO₄), after which the solvent was distilled off to yield ethyl 4,5,6,7-tetrahydro-4-oxo-5-propionylamino-3-propylthiobenzo[c]thiophene-1-carboxylate (2.70 g, 58.4%), which was then recrystallized from ethyl acetate-hexane. Colorless needle crystal. Melting point 191–192° C.

Examples 14 through 16

The compounds shown in Table 5 were obtained in the same manner as in Example 11.

TABLE 5

| Example No. | X | R¹ | Recovery (%) | Melting Point (° C.) | Recrystallizing Solvent |
|---|---|---|---|---|---|
| 14 | S | CH₃CH₂CH₂ | 87 | 200–201 | Chloroform-ethanol |
| 15 | S | CH₃CH₂CH₂CH₂ | 30 | 155–156 | Ethyl acetate-hexane |
| 16 | O | CH₃ | 11 | 181–182 | Ethyl acetate-hexane |

Example 17

A mixture of ethyl 5-acetylamino-4,5,6,7-tetrahydro-3-methylthio-4-oxobenzo[c]thiophene-1-carboxylate (2.46 g), phosphorus oxychloride (3.46 g) and toluene (80 ml) was refluxed under heating for 1.5 hours; the solution obtained was concentrated under reduced pressure, diluted with a saturated aqueous solution of sodium hydrogen carbonate (200 ml) and extracted with ethyl acetate. The organic layer was washed with water and dried (MgSO$_4$), after which the solvent was distilled off to yield ethyl 4,5-dihydro-2-methyl-8-methylthiothieno[3,4-g]benzoxazole-6-carboxylate (2.18 g, 94.0%), which was then recrystallized from ethyl acetate-hexane. Light-yellow needles. Melting point 131–132° C.

Example 18

A mixture of ethyl 5-acetylamino-4,5,6,7-tetrahydro-3-isopropylthio-4-oxobenzo[c]thiophene-1-carboxylate (1.00 g), phosphorus oxychloride (1.29 g) and toluene (30 ml) was refluxed under heating for 1.5 hours; the solution obtained was concentrated under reduced pressure, diluted with a saturated aqueous solution of sodium hydrogen carbonate and extracted with ethyl acetate. The organic layer was washed with water and dried (MgSO$_4$), after which the solvent was distilled off to yield ethyl 4,5-dihydro-8-isopropylthio-2-methylthieno[3,4-g]benzoxazole-6-carboxylate (0.95 g, 100%), which was then recrystallized from ethyl acetate-hexane. Yellow prisms. Melting point 62–63° C.

Examples 19 and 20

The compounds shown in Table 6 were obtained in the same manner as in Example 17.

TABLE 6

| Example No. | R$^1$ | A$^1$ | Recovery (%) | Melting Point (° C.) | Recrystallizing Solvent |
| --- | --- | --- | --- | --- | --- |
| 19 | CH$_3$CH$_2$CH$_2$ | CH$_3$ | 79 | 90–91 | Ethyl acetate-hexane |
| 20 | CH$_3$CH$_2$CH$_2$ | C$_2$H$_5$ | 83 | 67–68 | Ethyl acetate-hexane |

Example 21

A solution of sodium hydroxide (1.65 g) in water (3 ml) was added to a solution of benzamidine hydrochloride (5.38 g) in water (2 ml) at room temperature; a solution of ethyl 5-bromo-4,5,6,7-tetrahydro-3-methylthio-4-oxobenzo[c]thiophene-1-carboxylate (2.00 g) in chloroform (30 ml) was further added. The reaction mixture was refluxed under heating for 3 days, after which it was poured over water and extracted with ethyl acetate. The organic layer was washed with water and dried (MgSO$_4$), after which the solvent was distilled off. The residue was subjected to silica gel column chromatography and eluted with ethyl acetate-hexane (1:2, v/v) to yield ethyl 4,5-dihydro-8-methylthio-2-phenylthieno[3,4-e]benzimidazole-6-carboxylate (0.28 g, 13.2%), which was then recrystallized from ethyl acetate-ethanol. Brown prisms. Melting point 218–219° C.

Example 22

Ethyl 4,5-dihydro-2-methyl-8-methylthiothieno[3,4-e]benzothiazole-6-carboxylate (0.76 g) was suspended in a mixed solvent of ethanol (10 ml) and tetrahydrofuran (25 ml); a 2 N aqueous solution of sodium hydroxide (2.3 ml) was added at room temperature. After the reaction mixture was stirred at room temperature for 1 hour, the solution obtained was diluted with water (30 ml) and washed with diethyl ether. The water layer was acidified with 1 N hydrochloric acid (5 ml) and extracted with a mixed solvent of ethyl acetate and tetrahydrofuran. The ethyl acetate-tetrahydrofuran layer was washed with water and dried (MgSO$_4$), after which the solvent was distilled off to yield 4,5-dihydro-2-methyl-8-methylthiothieno[3,4-e]benzothiazole-6-carboxylic acid (0.35 g, 50%), which was then recrystallized from ethyl acetate-hexane. Brown prisms. Melting point 273–274° C.

Example 23

Ethyl 4,5-dihydro-8-methylthio-2-phenylthieno[3,4-e]benzothiazole-6-carboxylate (2.28 g) was suspended in a mixed solvent of ethanol (15 ml) and tetrahydrofuran (25 ml); a 2 N aqueous solution of sodium hydroxide (8.8 ml) was added at 50° C. After the reaction mixture was stirred at 50° C. for 4 hours, the solution obtained was poured over water (400 ml), acidified with concentrated hydrochloric acid, and extracted with ethyl acetate-tetrahydrofuran (3:1, v/v). The organic layer was washed with water and dried (MgSO$_4$), after which the solvent was distilled off to yield 4,5-dihydro-8-methylthio-2-phenylthieno[3,4-e]benzothiazole-6-carboxylic acid (2.08 g, 98.6%), which was then recrystallized from chloroform-methanol. Light-yellow prisms. Melting point 255–256° C. (decomposed).

Example 24

Ethyl 4,5-dihydro-2-phenyl-8-propylthiothieno[3,4-e]benzothiazole-6-carboxylate (3.62 g) was suspended in a mixed solvent of ethanol (25 ml) and tetrahydrofuran (15 ml); a 2 N aqueous solution of sodium hydroxide (13.3 ml) was added at 50° C. After the reaction mixture was stirred at 50° C. for 3 hours, the solution obtained was poured over water (400 ml), acidified with concentrated hydrochloric acid, and extracted with ethyl acetate-tetrahydrofuran (3:1, v/v). The organic layer was washed with water and dried (MgSO$_4$), after which the solvent was distilled off to yield 4,5-dihydro-2-phenyl-8-propylthiothieno[3,4-e]benzothiazole-6-carboxylic acid (3.33 g, 98.5%), which was then recrystallized from chloroform-methanol. Light-yellow prisms. Melting point 236–237° C. (decomposed).

Example 25

Ethyl 4,5-dihydro-8-methylthio-2-phenylfuro[3,4-e]benzothiazole-6-carboxylate (1.32 g) was suspended in a mixed solvent of ethanol (10 ml) and tetrahydrofuran (15 ml); a 2 N aqueous solution of sodium hydroxide (5.3 ml) was added at 50° C. After the reaction mixture was stirred at 50° C. for 1.5 hours, the solution obtained was poured over water (300 ml), acidified with concentrated hydrochloric acid, and extracted with ethyl acetate-tetrahydrofuran (3:1, v/v). The organic layer was washed with water and dried (MgSO$_4$), after which the solvent was distilled off to yield 4,5-dihydro-8-methylthio-2-phenylfuro[3,4-e]benzothiazole-6-carboxylic acid (1.14 g, 93.4%), which was then recrystallized from chloroform-methanol. Colorless prisms. Melting point 206–207° C. (decomposed).

Examples 26 through 31

The compounds shown in Table 7 were obtained in the same manner as in Example 23.

TABLE 7

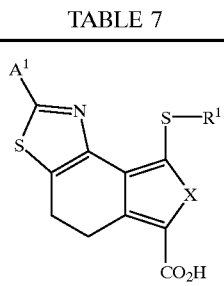

| Example No. | X | $R^1$ | $A^1$ | Recovery (%) | Melting Point (° C.) | Recrystallizing Solvent |
|---|---|---|---|---|---|---|
| 26 | S | $CH_3$ | $C_2H_5$ | 90 | 227–228 (decomposed) | Chloroform-methanol |
| 27 | S | $CH_3$ | $C_6H_5CH=CH$ (E) | 97 | 238–239 (decomposed) | Chloroform-methanol |
| 28 | S | $CH_3CH_2CH_2$ | $CH_3$ | 97 | 225–226 (decomposed) | Chloroform-methanol |
| 29 | S | $C_6H_5CH_2$ | $CH_3$ | 97 | 245–246 (decomposed) | Chloroform-methanol |
| 30 | S | $C_6H_5CH_2$ | $C_6H_5$ | 97 | 242–243 (decomposed) | Chloroform-methanol |
| 31 | O | $CH_3$ | $CH_3$ | 91 | 196–197 (decomposed) | Chloroform-methanol |

Example 32

Ethyl 4,5-dihydro-2-methyl-8-methylthiothieno[3,4-g]benzoxazole-6-carboxylate (1.88 g) was suspended in a mixed solvent of ethanol (15 ml) and tetrahydrofuran (10 ml); a 2 N aqueous solution of sodium hydroxide (9.1 ml) was added at 50° C. After the reaction mixture was stirred at 50° C. for 2 hours, the solution obtained was poured over water (300 ml), acidified with concentrated hydrochloric acid, and extracted with ethyl acetate-tetrahydrofuran (3:1, v/v). The organic layer was washed with water and dried ($MgSO_4$), after which the solvent was distilled off to yield 4,5-dihydro-2-methyl-8-methylthiothieno[3,4-g]benzoxazole-6-carboxylic acid (1.61 g, 94.2%), which was then recrystallized from chloroform-methanol. Light-yellow prisms. Melting point over 300° C.

Example 33

Ethyl 4,5-dihydro-8-isopropylthio-2-methylthieno[3,4-g]benzoxazole-6-carboxylate (0.71 g) was dissolved in ethanol (30 ml); a 2 N aqueous solution of sodium hydroxide (2.1 ml) was added at 50° C. After the reaction mixture was stirred at 50° C. for 1 hour, the solution obtained was poured over water, acidified with 1 N hydrochloric acid, and extracted with ethyl acetate. The organic layer was washed with water and dried ($MgSO_4$), after which the solvent was distilled off to yield 4,5-dihydro-8-isopropylthio-2-methylthieno[3,4-g]benzoxazole-6-carboxylic acid (0.57 g, 66%), which was then recrystallized from ethyl acetate-hexane. Yellow prisms. Melting point 277–278° C.

Examples 34 and 35

The compounds shown in Table 8 were obtained in the same manner as in Example 32.

TABLE 8

| Example No. | $R^1$ | $A^1$ | Recovery (%) | Melting Point (° C.) | Recrystallizing Solvent |
|---|---|---|---|---|---|
| 34 | $CH_3CH_2CH_2$ | $CH_3$ | 96 | 276–277 (decomposed) | Chloroform-methanol |
| 35 | $CH_3CH_2CH_2$ | $C_2H_5$ | 95 | 248–249 (decomposed) | Ethyl acetate-hexane |

Example 36

4,5-Dihydro-2-methyl-8-methylthiothieno[3,4-e]benzothiazole-6-carboxylic acid (0.30 g) was dissolved in tetrahydrofuran (20 ml); oxalyl chloride (0.26 g) and then N,N-dimethylformamide (1 drop) were added. After this mixture was stirred at room temperature for 1.5 hours, it was concentrated under reduced pressure. The residue was dissolved in tetrahydrofuran (20 ml); concentrated aqueous ammonia (2 ml) was added. After the reaction mixture was stirred at room temperature for 1.5 hours, it was poured over water and stirred at room temperature for 15 minutes; the crystal precipitated was collected by filtration to yield 4,5-dihydro-2-methyl-8-methylthiothieno[3,4-e]benzothiazole-6-carboxamide (0.29 g, 97%), which was then recrystallized from chloroform-ethanol. Yellow prisms. Melting point 269–270° C.

Example 37

4,5-Dihydro-2-phenyl-8-propylthiothieno[3,4-e]benzothiazole-6-carboxylic acid (1.85 g) was suspended in tetrahydrofuran (50 ml); oxalyl chloride (0.91 g) and then N,N-dimethylformamide (1 drop) were added. After this mixture was stirred at room temperature for 2 hours, it was concentrated under reduced pressure. The residue was suspended in tetrahydrofuran (15 ml) and cooled with ice; concentrated aqueous ammonia (12.0 ml) was added. After the reaction mixture was stirred at room temperature for 1 hour, it was poured over water (450 ml) and extracted with ethyl acetate-tetrahydrofuran (3:1, v/v). The organic layer was washed with water and dried ($MgSO_4$), after which it was treated with activated charcoal and the solvent was distilled off to yield 4,5-dihydro-2-phenyl-8-propylthiothieno[3,4-e]benzothiazole-6-carboxamide (1.34 g, 72.4%), which was then recrystallized from chloroform-ethanol. Yellow prisms. Melting point 203–204° C.

Examples 38 through 45

The compounds shown in Table 9 were obtained in the same manner as in Example 37.

Example 46

4,5-Dihydro-2-methyl-8-methylthiothieno[3,4-g]benzoxazole-6-carboxylic acid (0.47 g) was suspended in tetrahydrofuran (15 ml); oxalyl chloride (0.32 g) and then N,N-dimethylformamide (6 μl) were added. After this mixture was stirred at room temperature for 2 hours, it was concentrated under reduced pressure. The residue was suspended in tetrahydrofuran (5 ml) and cooled with ice; concentrated aqueous ammonia (4.0 ml) was added. After the reaction mixture was stirred at room temperature for 1 hour, it was poured over water (150 ml) and extracted with ethyl acetate-tetrahydrofuran (3:1, v/v). The organic layer was washed with water and dried ($MgSO_4$), after which the solvent was distilled off to yield 4,5-dihydro-2-methyl-8-methylthiothieno[3,4-g]benzoxazole-6-carboxamide (0.27 g, 57%), which was then recrystallized from chloroform-methanol. Light-yellow needles. Melting point over 300° C.

Example 47

4,5-Dihydro-8-isopropylthio-2-methylthieno[3,4-g]benzoxazole-6-carboxylic acid (0.40 g) was dissolved in tetrahydrofuran (30 ml); oxalyl chloride (0.23 g) and then N,N-dimethylformamide (1 drop) were added. After this mixture was stirred at room temperature for 2 hours, it was concentrated under reduced pressure. The residue was dissolved in tetrahydrofuran (30 ml); concentrated aqueous ammonia (3 ml) was added. After the reaction mixture was stirred at room temperature for 1 hour, it was poured over water and extracted with ethyl acetate. The organic layer was washed with water and dried ($MgSO_4$), after which the solvent was distilled off to yield 4,5-dihydro-8-isopropylthio-2-methylthieno[3,4-g]benzoxazole-6-carboxamide (0.31 g, 78%), which was then recrystallized from chloroform-ethanol. Colorless prisms. Melting point 230–231° C.

Examples 48 and 49

The compounds shown in Table 10 were obtained in the same manner as in Example 46.

TABLE 9

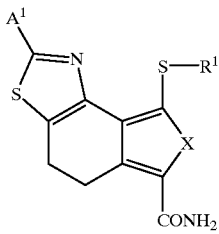

| Example No. | X | $R^1$ | $A^1$ | Recovery (%) | Melting Point (° C.) | Recrystallizing Solvent |
|---|---|---|---|---|---|---|
| 38 | S | $CH_3$ | $C_2H_5$ | 81 | 202–203 | Chloroform-methanol |
| 39 | S | $CH_3$ | $C_6H_5$ | 81 | 242–243 | Chloroform-methanol |
| 40 | S | $CH_3$ | $C_6H_5CH=CH$ (E) | 81 | 219–220 | Chloroform-methanol |
| 41 | S | $CH_3CH_2CH_2$ | $CH_3$ | 82 | 224–225 | Chloroform-methanol |
| 42 | S | $C_6H_5CH_2$ | $CH_3$ | 79 | 203–204 | Chloroform-methanol |
| 43 | S | $C_6H_5CH_2$ | $C_6H_5$ | 76 | 227–228 | Chloroform-methanol |
| 44 | O | $CH_3$ | $CH_3$ | 61 | 196–197 | Ethanol-hexane |
| 45 | O | $CH_3$ | $C_6H_5$ | 82 | 230–231 | Chloroform-methanol |

TABLE 10

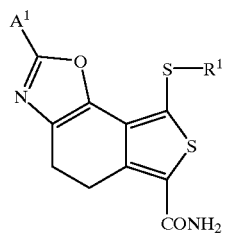

| Example No. | R¹ | A¹ | Recovery (%) | Melting Point (° C.) | Recrystallizing Solvent |
|---|---|---|---|---|---|
| 48 | CH₃CH₂CH₂ | CH₃ | 75 | 231–232 | Chloroform-ethanol |
| 49 | CH₃CH₂CH₂ | C₂H₅ | 61 | 203–204 | Ethanol-hexane |

Example 50

4,5-Dihydro-8-methylthio-2-phenylthieno[3,4-e]benzothiazole-6-carboxylic acid (0.43 g) was suspended in tetrahydrofuran (15 ml); oxalyl chloride (0.23 g) and then N,N-dimethylformamide (6 µl) were added. After this mixture was stirred at room temperature for 2 hours, it was concentrated under reduced pressure. The residue was suspended in tetrahydrofuran (5 ml) and cooled with ice; a 70% aqueous solution of ethylamine (4.0 ml) was added. After the reaction mixture was stirred at room temperature for 1 hour, it was poured over water (150 ml) and extracted with ethyl acetate-tetrahydrofuran (3:1, v/v). The organic layer was washed with water and dried (MgSO₄), after which the solvent was distilled off to yield N-ethyl-4,5-dihydro-8-methylthio-2-phenylthieno[3,4-e]benzothiazole-6-carboxamide (0.35 g, 76%), which was then recrystallized from chloroform-ethanol. Yellow needles. Melting point 211–212° C.

Examples 51 through 54

The compounds shown in Table 11 were obtained in the same manner as in Example 50.

TABLE 11

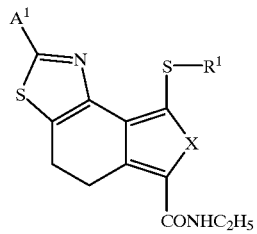

| Example No. | X | R¹ | A¹ | Recovery (%) | Melting Point (° C.) | Recrystallizing Solvent |
|---|---|---|---|---|---|---|
| 51 | S | CH₃ | C₂H₅ | 76 | 142–143 | Ethanol-hexane |
| 52 | S | CH₃ | C₆H₅CH=CH (E) | 82 | 216–217 | Chloroform-ethanol |
| 53 | S | CH₃CH₂CH₂ | CH₃ | 75 | 128–129 | Ethanol-hexane |
| 54 | S | CH₃CH₂CH₂ | C₆H₅ | 71 | 154–155 | Ethanol-hexane |

Examples 55 through 57

The compounds shown in Table 12 were obtained in the same manner as in Example 50.

TABLE 12

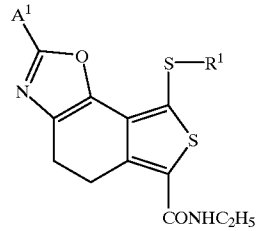

| Example No. | R | A¹ | Recovery (%) | Melting Point (° C.) | Recrystallizing Solvent |
|---|---|---|---|---|---|
| 55 | CH₃ | CH₃ | 60 | 175–176 | Ethanol-hexane |
| 56 | CH₃CH₂CH₂ | CH₃ | 68 | 117–118 | Ethanol-hexane |
| 57 | CH₃CH₂CH₂ | C₂H₅ | 54 | 91–92 | Ethanol-hexane |

Example 58

2-Ethyl-4,5-dihydro-8-methylthiothieno[3,4-e]benzothiazole-6-carboxylic acid (0.47 g) was suspended in tetrahydrofuran (15 ml); oxalyl chloride (0.29 g) and then N,N-dimethylformamide (6 µl) were added. After this mixture was stirred at room temperature for 2 hours, it was concentrated under reduced pressure. The residue was suspended in tetrahydrofuran (8 ml); this suspension was added to a solution of diethyl 4-aminobenzylphosphonate (0.40 g), triethylamine (0.17 g) and tetrahydrofuran (15 ml) at room temperature. After the reaction mixture was stirred at room temperature for 1 hour, it was poured over water (150 ml) and extracted with ethyl acetate-tetrahydrofuran (3:1, v/v). The organic layer was washed with 1 N hydrochloric acid, water, a saturated aqueous solution of sodium hydrogen carbonate and water in that order, and dried (MgSO₄), after which the solvent was distilled off to yield N-[4-(diethoxyphosphorylmethyl)phenyl]-2-ethyl-4,5-dihydro-8-methylthiothieno[3,4-e]benzothiazole-6-carboxamide (0.69 g, 85%), which was then recrystallized from ethanol-hexane. Yellow needles. Melting point 179–180° C.

Examples 59 through 64

The compounds shown in Table 13 were obtained in the same manner as in Example 58.

TABLE 13

| Example No. | X | R¹ | A¹ | Recovery (%) | Melting Point (° C.) | Recrystallizing Solvent |
|---|---|---|---|---|---|---|
| 59 | S | CH₃ | C₆H₅ | 83 | 215–216 | Chloroform-ethanol |
| 60 | S | CH₃ | C₆H₅CH=CH (E) | 85 | 208–209 | Chloroform-ethanol |
| 61 | S | CH₃CH₂CH₂ | CH₃ | 84 | 180–181 | Chloroform-ethanol |
| 62 | S | CH₃CH₂CH₂ | C₆H₅ | 78 | 173–174 | Chloroform-ethanol |
| 63 | O | CH₃ | CH₃ | 63 | 155–156 | Ethanol-hexane |
| 64 | O | CH₃ | C₆H₅ | 78 | 198–199 | Chloroform-ethanol |

Example 65

4,5-Dihydro-2-methyl-8-methylthiothieno[3,4-g]benzoxazole-6-carboxylic acid (0.37 g) was suspended in tetrahydrofuran (15 ml); oxalyl chloride (0.25 g) and then N,N-dimethylformamide (6 μl) were added. This reaction mixture was stirred at room temperature for 2 hours, after which it was concentrated under reduced pressure. The residue was suspended in tetrahydrofuran (8 ml); this suspension was added to a solution of diethyl 4-aminobenzylphosphonate (0.35 g), triethylamine (0.15 g) and tetrahydrofuran (15 ml) at room temperature. After being stirred at room temperature for 1 hour, the reaction mixture was poured over water (150 ml) and extracted with ethyl acetate-tetrahydrofuran (3:1, v/v). The organic layer was washed with 1 N hydrochloric acid, water, a saturated aqueous solution of sodium hydrogen carbonate and water in that order, and dried (MgSO₄), after which the solvent was distilled off to yield N-[4-(diethoxyphosphorylmethyl)phenyl]-4,5-dihydro-2-methyl-8-methylthiothieno[3,4-g]benzoxazole-6-carboxamide (0.52 g, 78%), which was then recrystallized from chloroform-ethanol. Light-yellow needles. Melting point 197–198° C.

Examples 66 and 67

The compounds shown in Table 14 were obtained in the same manner as in Example 65.

TABLE 14

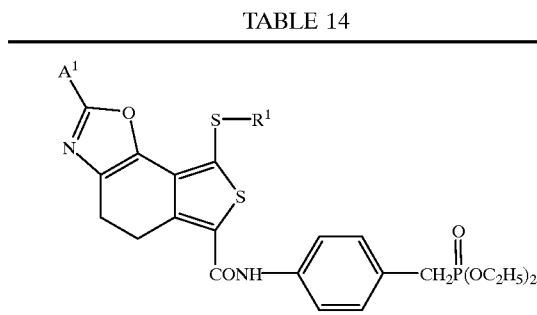

| Example No. | R¹ | A¹ | Recovery (%) | Melting Point (° C.) | Recrystallizing Solvent |
|---|---|---|---|---|---|
| 66 | CH₃CH₂CH₂ | CH₃ | 69 | 134–135 | Ethanol-hexane |
| 67 | CH₃CH₂CH₂ | C₂H₅ | 72 | 128–129 | Ethanol-hexane |

Example 68

A mixture of ethyl 4,5-dihydro-8-methylthio-2-phenylthieno[3,4-e]benzimidazole-6-carboxylate (0.50 g), a 10% (w/w) ammonia solution (30 ml) in methanol and tetrahydrofuran (30 ml) was heated in a sealed tube at 100° C. for 3 days. The reaction mixture was poured over water and extracted with ethyl acetate-tetrahydrofuran (3:1, v/v). The organic layer was washed with water and dried (MgSO$_4$), after which the solvent was distilled off. The residue was subjected to silica gel column chromatography and eluted with chloroform-methanol (30:1, v/v) to yield 4,5-dihydro-8-methylthio-2-phenylthieno[3,4-e]benzimidazole-6-carboxamide (65 mg, 14%), which was then recrystallized from ethanol. Colorless prisms. Melting point 206–207° C.

Example 69

Ethyl 4,5,6,7-tetrahydro-3-methylthio-4-oxobenzo[c]thiophene-1-carboxylate (5.47 g) was dissolved in chloroform (130 ml) and added dropwise to a solution of phosphorus oxychloride (50.71 g) in N,N-dimethylformamide (40 ml) at 0° C. This mixture was stirred at room temperature, after which it was refluxed under heating in a nitrogen stream for 4.5 hours. The reaction mixture was poured over ice water and extracted with ethyl acetate. The organic layer was washed with water and dried (MgSO$_4$), after which the solvent was distilled off to yield ethyl 4-chloro-5-formyl-6,7-dihydro-3-methylthiobenzo[c]thiophene-1-carboxylate (4.72 g, 73.8%), which was then recrystallized from ethyl acetate. Yellow prisms. Melting point 79–80° C.

Example 70

To a mixture of ethyl 4-chloro-5-formyl-6,7-dihydro-3-methylthiobenzo[c]thiophene-1-carboxylate (3.00 g), triethylamine (1.44 g) and pyridine (25 ml), ethyl thioglycolate (1.37 g) was added at 0° C., followed by stirring at 0° C. for 1.5 hours. The reaction mixture was concentrated under reduced pressure; the residue was poured over water and extracted with ethyl acetate. The organic layer was washed with 1 N hydrochloric acid and water in that order and dried (MgSO$_4$), after which the solvent was distilled off. The residue was subjected to silica gel column chromatography and eluted with ethyl acetate-hexane (1:7 to 1:5, v/v) to yield ethyl 4-ethoxycarbonylmethylthio-5-formyl-6,7-dihydro-3-methylthiobenzo[c]thiophene-1-carboxylate (3.07 g, 81.0%), which was then recrystallized from ethyl acetate-hexane. Yellow prisms. Melting point 102–103° C.

Example 71

Ethyl 4-ethoxycarbonylmethylthio-5-formyl-6,7-dihydro-3-methylthiobenzo[c]thiophene-1-carboxylate (0.30 g) was dissolved in acetic anhydride (10 ml) and refluxed under heating for 11 hours, after which it was concentrated under reduced pressure. The residue was poured over water and extracted with ethyl acetate. The organic layer was washed with a saturated aqueous solution of sodium hydrogen carbonate and water in that order and dried (MgSO$_4$), after which the solvent was distilled off. The residue was subjected to silica gel column chromatography and eluted with ethyl acetate-hexane (1:7, v/v) to yield diethyl 4,5-dihydro-8-methylthiobenzo[2,1-c:3,4-b']dithiophene-2,6-dicarboxylate (0.15 g, 52%), which was then recrystallized from ethyl acetate-hexane. Yellow prisms. Melting point 107–108° C.

Example 72

Diethyl 4,5-dihydro-8-methylbenzo[2,1-c:3,4-b]dithiophene-2,6-dicarboxylate (0.36 g) was dissolved in a mixed solvent of ethanol (20 ml) and tetrahydrofuran (10 ml); an aqueous solution of potassium hydroxide (0.37 g) in water (5 ml) was added. The reaction mixture was stirred at room temperature for 22 hours, and the solution obtained was poured over water, acidified with 1 N hydrochloric acid, and extracted with ethyl acetate-tetrahydrofuran. The organic layer was washed with water and dried (MgSO$_4$), after which the solvent distilled off to yield 4,5-dihydro-8-methylthiobenzo[2,1-c:3,4-b']dithiophene-2,6-dicarboxylic acid (0.29 g, 85%), which was then recrystallized from ethyl acetate-tetrohydrofuran. Light-yellow prisms, Melting point over 300° C.

Example 73

4,5-Dihydro-8-methylthiobenzo[2,1-c:3,4-b']dithiophene-2,6-dicarboxylic acid (0.28 g) was dissolved in tetrahydrofuran (60 ml); oxalyl chlorid (0.19 ml) was added and then N,N-dimethylformamide (1 drop) was added. The reaction mixture was stirred at room temperature for 2 hours, after which it was concentrated under reduced pressure. The residue was dissolved in tetrahydrofuran (15 ml) and a concentrated aqueous ammonia (3 ml) was added. After stirring at room temperature for 1 hour, the reaction mixture was poured over water and extracted with chloroform-methanol. The organic layer was washed with water and dried (MgSO$_4$), after which the solvent was distilled off to yield 4,5-dihydro-8-methylthiobenzo[2,1-c:3,4-b']dithiophene-2,6-dicarboxamide (0.26 g, 92%), which was then recrystallized from chloroform-methanol. Colorless prisms. Melting point over 300° C.

Example 74

4,5-Dihydro-8-methylthiobenzo[2,1-c:3,4-b']dithiophene-2,6-dicarboxylic acid (0.30 g) was dissolved in tetrohydrofuran (60 ml); oxalyl chloride (0.20 ml) and then N,N-dimethylformamide (1 drop) were added. After this mixture was stirred at room temperature for 2 hours, it was concentrated under reduced pressure. The residue was dissolved in tetrahydrofuran (15 ml); diethyl 4-aminobenzylphosphonate (0.52 g) and triethylamine (0.32 ml) were added. After the reaction mixture was stirred at room temperature for 1 hour, it was poured over water and extracted with ethyl acetate. The organic layer was washed with 1 N hydrochloric acid, water and saturated aqueous sodium hydrogen carbonate in that order and dried (MgSO$_4$), after which the solvent was distilled off to yield N,N-bis[4-(diethoxyphosphorylmethyl)phenyl]-4,5-dihydro-8-methylthiobenzo[2,1-c:3,4-b']dithiophene-2,6-dicarboxamide (0.46 g, 64%), which was then recrystallized from chloroform-ethanol. Yellow prisms. Melting point 262–263° C.

Example 75

Ethyl 4-chloro-5-formyl-6,7-dihydro-3-methylthiobenzo[c]thiophene-1-carboxylate (1.32 g), methyl α-mercaptophenyl acetate (0.76 g) and potassium carbonate (0.69 g) were added to N,N-dimethylformamide (15 ml). The mixture was stirred at room temperature for 2 hours. The reaction mixture was poured over water, and extracted with ethyl acetate. The organic layer was washed with water and dried (MgSO$_4$), after which the solvent was distilled off. The residue was subjected to silica gel column chromatography and eluted with ethyl acetate-hexane (1:5, v/v) to yield yellow powder. The powder was dissolved in ethanol (10 ml), to which an aqueous sodium hydroxide (0.10 g) in water (2 ml) was added. The obtained solution was stirred at 60° C. for 7 hours. To the reaction solution was added concentrated hydrochloric acid (1 drop). After the mixture was poured over water, it was extracted-with ethyl acetate. The organic layer was washed with water and dried (MgSO$_4$), after which the solvent was distilled off. The residue was subjected to silica gel column chromatography and eluted with chloroform-methanol to yield 4,5-dihydro-8-methylthio-2-phenylbenzo[2,1-c:3,4-b']dithiophene-6-carboxylic acid, which was then recrystallized from ethyl acetate-hexane. Yellow prisms. Melting point 215–217° C.

Example 76

4,5-Dihydro-8-methylthio-2-phenylbenzo[2,1-c:3,4-b'] dithiophene-6-carboxylic acid (0.50 g) was dissolved in tetrahydrofuran (10 ml); oxazolyl chloride (0.15 ml) and then N,N-dimethylformamide (one drop) were added. After the mixture was stirred at room temperature for 2 hours, it was concentrated under reduced pressure. The residue was dissolved in tetrahydrofuran (30 ml); concentrated aqueous ammonia (5 ml) was added. After the reaction mixture was stirred at room temperature for one hour, it was poured over water and extracted with chloroform-methanol the organic layer was washed with water and dried (MgSO$_4$), after which the solvent was distilled off to yield 4,5-dihydro-8-methylthio-2-phenylbenzo[2,1-c:3,4-b']dithiophene-6-carboxamide (0.28 g, 56%), which was recrystallized from ethanol. Melting point 192–193° C.

Example 77

4,5-Dihydro-8-methylthio-2-phenylbenzo[2,1-c:3,4-b'] dithiophene-6-carboxylic acid (0.50 g) was dissolved in tetrahydrofuran (30 ml); oxalyl chloride (0.15 ml) and then N,N-dimethylformamide (one drop) were added. After the mixture was stirred at room temperature for 2 hours, it was concentrated under reduced pressure. The residue was dissolved in tetrahydrofuran (20 ml); diethyl 4-aminobenzylphosphonate (0.37 g) and triethylamine (0.23 ml) were added. After the reaction mixture was stirred at room temperature for 1 hour, it was poured over water and extracted with ethyl acetate-tetrahydrofuran. The organic layer was washed with 1 N hydrochloric acid, water and saturated aqueous potassium hydrogen carbonate in that order and dried (MgSO$_4$), after which the solvent was distilled off to yield N-[4-(diethoxyphospholylmethyl) phenyl]-4,5-dihydro-8-methylthio-2-phenylbenzo[2,1-c:3, 4-b']dithiophene-6-carboxamide (0.44 g, 54%), which was recrystallized from ethanol-hexane.

Melting point 178–180° C.

Examples 78 through 81

The compounds shown in Table 15 were obtained in the same manner as in Example 1.

TABLE 15

| Example No. | $R^1$ | $A^1$ | Recovery (%) | Melting Point (° C.) | Recrystallizing Solvent |
|---|---|---|---|---|---|
| 78 | CH$_3$ | 4-Py | 88 | 248–249 | Chloroform |
| 79 | CH$_3$ | 4-Cl-Ph | 43 | 183–184 | Ethyl acetate-hexane |
| 80 | CH$_3$CH$_2$CH$_2$ | 4-Cl-Ph | 23 | 136–137 | Ethyl acetate-hexane |
| 81 | CH$_3$CH$_2$CH$_2$ | 4-Py | 41 | 165–166 | Chloraform |

4-Py: 4-Pyridyl, 4-Cl-Ph: 4-Chlorophenyl

Examples 82 through 85

The compounds shown in Table 16 were obtained by the same manner as in Example 22.

TABLE 16

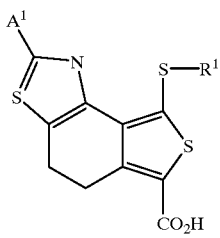

| Example No. | R¹ | A¹ | Recovery (%) | Melting Point (° C.) | Recrystallizing Solvent |
|---|---|---|---|---|---|
| 82 | $CH_3$ | 4-Py | 87 | >300 | Chloroform |
| 83 | $CH_3$ | 4-Cl-Ph | 94 | 275–276 | Ethyl acetate-tetrahydrofuran |
| 84 | $CH_3CH_2CH_2$ | 4-Cl-Ph | 96 | 243–244 | Ethyl acetate-hexane |
| 85 | $CH_3CH_2CH_2$ | 4-Py | 100 | 298–299 | Tetrahydrofuran |

4-Py: 4-Pyridyl, 4-Cl-Ph: 4-Chlorophenyl

Examples 86 through 89

The compounds shown in Table 17 were obtained by the same manner as in Example 37.

TABLE 17

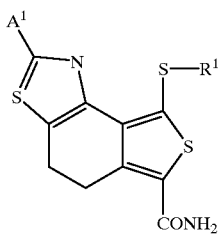

| Example No. | R¹ | A¹ | Recovery (%) | Melting Point (° C.) | Recrystallizing Solvent |
|---|---|---|---|---|---|
| 86 | $CH_3$ | 4-Py | 36 | 159–160 | Ethyl acetate-tetrahydrofuran |
| 87 | $CH_3$ | 4-Cl-Ph | 98 | 206–207 | Ethyl acetate-tetrahydrofuran |
| 88 | $CH_3CH_2CH_2$ | 4-Cl-Ph | 96 | 196–197 | Ethyl acetate-hexane |
| 89 | $CH_3CH_2CH_2$ | 4-py | 72 | 224–225 | Chloroform |

4-Py: 4-Pyridyl, 4-Cl-Ph: 4-Chlorophenyl

Examples 90 through 92

The compounds shown in Table 18 were obtained by the same manner as in Example 58.

TABLE 18

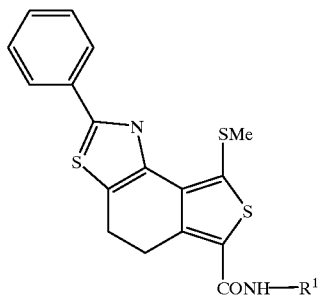

| Example No. | R¹ | Recovery (%) | Melting Point (° C.) | Recrystallizing Solvent |
|---|---|---|---|---|
| 90 | CH₂—(benzo[1,3]dioxol-5-yl) | 97 | 236–237 | Chloroform-methanol |
| 91 | CH₂—(pyridin-4-yl) | 89 | 189–190 | Ethyl acetate-hexane |
| 92 | (pyridin-3-yl) | 91 | 230–231 | Chloroform |

Example 93

N,O-Dimethylhydroxylamine hydrochloride (0.56 g) was dissolved in N,N-dimethylformamide (40 ml); to the solution was added triethylamine (0.84 ml). After the mixture was stirred at room temperature for 30 minutes, 4,5-dihydro-8-methylthio-2-phenylthieno[3,4-e]benzothiazole-6-carboxylic acid (1.7 g), 1-hydroxybenzotriazole (HOBt) (0.84 g) and 1-ethyl-3-(3-dimethylaminopropyl) carbodimide hydrochloride (WSC) (1.08 g) were added thereto in that order.

After the reaction mixture was stirred at room temperature for 13 hours, it was poured over 1N hydrochloric acid and extracted with ethyl acetate. The organic layer was washed with water and dried (MgSO₄), after which the solvent was distilled off to yield N-methoxy-N-methyl-4,5-dihydro-8-methylthio-2-phenylthieno[3,4-e]benzothiazole-6-carboxamide (2.03 g, 100%), which was recrystallized from ethyl acetate-hexane. Yellow prisms. Melting point 157–158° C.

Preparation Examples

A cell differentiation induction factor action enhancer (e.g., prophylactic/therapeutic agents for osteoporosis, bone fractures and diseases based on nerve degeneration) and anti-matrix metalloprotease agent (e.g., prophylactic/therapeutic agents for osteoarthritis) containing an inventive compound represented by general formula (I) or a salt thereof as an active ingredient can, for example, be produced with the following formulations:

| 1. Capsules | |
|---|---|
| (1) Compound obtained in Example 46 | 10 mg |
| (2) Lactose | 90 mg |
| (3) Microcrystalline cellulose | 70 mg |
| (4) Magnesium stearate | 10 mg |
| 1 capsule | 180 mg |

Components (1), (2) and (3) and a half portion of component (4) were mixed and granulated. To these granules, the remaining portion of component (4) was added, and the whole mixture packed in a gelatin capsule.

| 2. Tablets | |
|---|---|
| (1) Compound obtained in Example 50 | 10 mg |
| (2) Lactose | 35 mg |
| (3) Corn starch | 150 mg |
| (4) Microcrystalline cellulose | 30 mg |
| (5) Magnesium stearate | 5 mg |
| 1 tablet | 230 mg |

Components (1), (2) and (3), a two-third portion of component (4) and a half portion of component (5) were mixed and granulated. To these granules, the remaining portions of components (4) and (5) added, and the whole mixture tableted by compressive tableting.

INDUSTRIAL APPLICABILITY

The compound of the present invention, represented by general formula (I), or a salt thereof, possesses potent osteoblast-activating activity and BMP action-enhancing activity, for example, and is useful as a prophylactic/therapeutic agent for metabolic bone diseases, including osteoporosis. Also, osteogenesis promoters possessing such activity are applicable to the prevention and treatment of bone fractures, bone defects and bone diseases such as osteoarthritis in the field of orthopaedics. Furthermore, in the field of dentistry, it is expected to have such effects as repair of periodontal tissue defects due to periodontal diseases, stabilization of artificial tooth roots, mandibular ridge formation and cleft palate repair. Also, the compound of the present invention, represented by general formula (I), or a salt thereof, possesses neurotrophic factor action-enhancing activity, and is useful in the treatment and prevention of various diseases based on nerve degeneration such as Alzheimer's dementia, general senile dementia, motor neuron, psychological disorders such as depression disorders (amyotrophic lateral sclerosis etc.) and diabetic peripheral neuropathy. Furthermore, the compound of the present invention, represented by general formula (I), or a salt thereof, possesses anti-MMP activity, and is useful in the treatment and prevention of MMP-involved diseases such as osteoarthritis, rheumatoid arthritis, arteriosclerosis and cancer metastasis.

What is claimed is:

1. A compound of the formula:

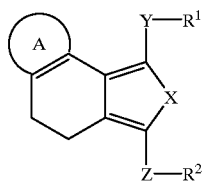

wherein

X represents a sulfur atom or an oxygen atom;

Y represents an optionally oxidized sulfur atom or an oxygen atom;

Z represents a bond or a divalent hydrocarbon group;

$R^1$ represents an optionally substituted hydrocarbon group;

$R^2$ represents an optionally amidated or esterified carboxyl group; and ring A represents an optionally substituted pyrazole ring; or a salt thereof, with the proviso that when X is S, —Y—$R^1$ is —S—$CH_3$, and —Z—$R^2$ is —$COOC_2H_5$, A does not represent

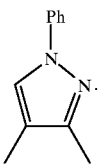

2. A compound according to claim 1 wherein ring A is an ring.

3. A compound according to claim 2, wherein Y is a sulfur atom.

4. A compound according to claim 3 wherein Z is a bond.

5. A compound according to claim 3, 4, or 1 wherein $R^1$ is a $C_{1-8}$ alkyl group, a $C_{6-10}$ aryl group or $C_{7-14}$ aralkyl group.

6. A compound according to claim 3, 4, or 1 wherein R–is a carboxyl group, a $C_{1-8}$ alkoxy-carbonyl group, a carbamoyl group, an N—($C_{1-8}$ alkoxy)carbamoyl group or an N—($C_{1-8}$ alkyl), N—($C_{1-8}$alkoxy)carbamoyl group or an N-carbomoyl group or an N—($C_{1-8}$ alkyl), N—($C_{1-8}$ alkoxy) carbamoyl group.

7. A compound according to claim 6 wherein $R^2$ is a carboxyl group, a carbamoyl group or an N—($C_{1-8}$ alkyl) carbamoyl group.

8. A compound according to claim 1 wherein

X is a sulfur atom or an oxygen atom,

Y is a sulfur atom,

Z is a bond, $R^1$ is a $C_{1-8}$ alkyl group, a $C_{b\ 6-10}$ aryl group or a $C_{7-14}$ aralkyl group, and $R^2$ is a carboxyl group, a $C_{1-8}$ alkoxy-carbonyl group, a carbomoyl group, an N—($C_{1-6}$ alkyl)carbamoyl group, an —carbamoyl group or an N—($C_{1-8}$ alkyl), N—($C_{1-8}$ alkoxy)carbamoyl group.

9. A pharmaceutical composition which comprises an effective amount of the compound according to claim 1 and a pharmaceutical acceptable carrier.

10. A method for treating osteoporosis, bone fractures, osteoarthritis, rheumatoid-arthritis, arteriosclerosis, cancer metastasis in bone or a disease based on nerve degeneration comprising administering a compound according to claim 1 to a warm blooded animal in need thereof.

11. A method for enhancing cell differentiation induction factor activity which comprises administering a compound according to claim 1 to a mammal in need thereof.

12. A method of inducing anti-matrix metalloprotease activity comprising administering a compound according to claim 1 to a mammal in need thereof.

13. A process of manufacturing a pharmaceutical composition, comprising admixing a compound according to claim 1 with a pharmaceutically acceptable excipient.

* * * * *

UNITED STATES PATENT AND TRADEMARK OFFICE
CERTIFICATE OF CORRECTION

PATENT NO. : 6,391,905 B1
DATED : May 21, 2002
INVENTOR(S) : Tsuneo Yasuma et al.

It is certified that error appears in the above-identified patent and that said Letters Patent is hereby corrected as shown below:

Column 29,
Line 15, "known." should read -- known --.

Column 33,
Line 37, "$MC_3T3-E1$" should read -- MC3T3-E1 --.

Column 34,
Line 4, "$PC_{12}$" should read -- PC12 --;
Line 40, "*p<0.05;" should read -- *, p<0.05; --; and
Line 41, "p<0.01" should read -- , p<0.01 --.

Column 53,
Line 16, "extracted-with" should read -- extracted with --; and
Line 63, "cholorform-methanol the" should read -- cholorform-methanol. The --.

Column 60,
Lines 9 and 25, "claim 1" should read -- claim 1, --;
Line 10, "ring." should read -- unsubstituted pyrazole ring. --;
Line 13, "claim 3" should read -- claim 3, --;
Line 14, "or 1" should read -- or 1, --;
Line 17, "or 1 wherein R–is" should read -- or 1, wherein $R^2$ is --;
Line 22, "claim 6" should read -- claim 6, --; and
Line 29, "$C_{b\ 6-10}$" should read -- $C_{6-10}$ --.

Signed and Sealed this

Nineteenth Day of November, 2002

*Attest:*

JAMES E. ROGAN
*Attesting Officer*       *Director of the United States Patent and Trademark Office*